United States Patent
Hori et al.

(10) Patent No.: US 9,057,688 B2
(45) Date of Patent: Jun. 16, 2015

(54) DETECTION DEVICE FOR DETECTING A TEST SUBSTANCE

(75) Inventors: Nobuyasu Hori, Kobe (JP); Hiroya Kirimura, Kobe (JP)

(73) Assignee: SYSMEX CORPORATION, Hyogo (JP)

(*) Notice: Subject to any disclaimer, the term of this patent is extended or adjusted under 35 U.S.C. 154(b) by 0 days.

(21) Appl. No.: 13/277,712

(22) Filed: Oct. 20, 2011

(65) Prior Publication Data
US 2012/0103836 A1    May 3, 2012

(30) Foreign Application Priority Data

Oct. 29, 2010  (JP) ................... 2010-244606
Oct. 13, 2011  (JP) ................... 2011-225926

(51) Int. Cl.
*G01N 27/416*  (2006.01)
*G01N 27/30*   (2006.01)
*G01N 33/543*  (2006.01)

(52) U.S. Cl.
CPC .......... *G01N 27/305* (2013.01); *G01N 33/5438* (2013.01)

(58) Field of Classification Search
CPC .................. G01N 33/5438; G01N 27/305
USPC .................. 204/403.01–403.15; 205/792
See application file for complete search history.

(56) References Cited

U.S. PATENT DOCUMENTS

| | | | | |
|---|---|---|---|---|
| 4,534,099 A | * | 8/1985 | Howe | 438/98 |
| 2009/0294305 A1 | | 12/2009 | Bekki et al. | |
| 2010/0108539 A1 | * | 5/2010 | Iwanaga et al. | 205/687 |

FOREIGN PATENT DOCUMENTS

CN    101317087 A    12/2008

* cited by examiner

*Primary Examiner* — Keith Hendricks
*Assistant Examiner* — Kourtney S Carlson
(74) *Attorney, Agent, or Firm* — Sughrue Mion, PLLC

(57) ABSTRACT

A detection device for detecting a test substance which is capable of detecting a test substance and a sample substance with high sensitivity, an electrode substrate, a working electrode, an inspection tip, a method of detecting a test substance, and a method of detecting a sample substance are provided in which a reflective part (reflective layer) is disposed on the working electrode so as to reflect excitation light emitted from a light source and passing through the working electrode toward the working electrode.

17 Claims, 26 Drawing Sheets

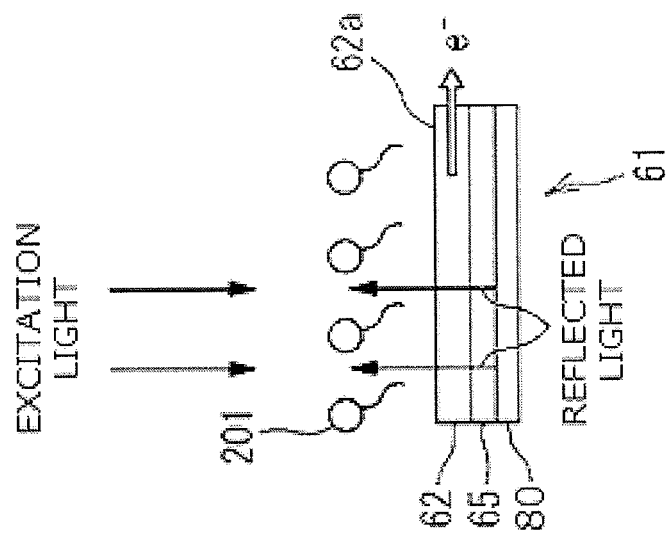
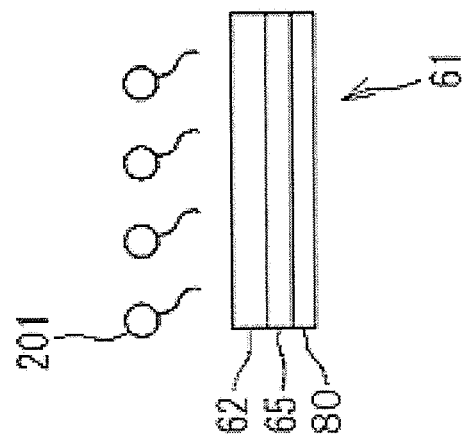
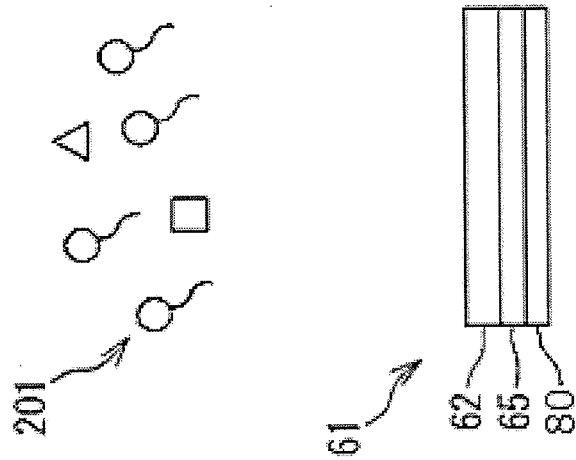

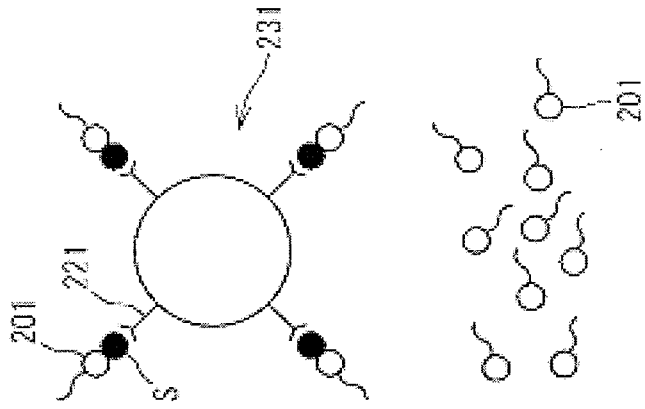
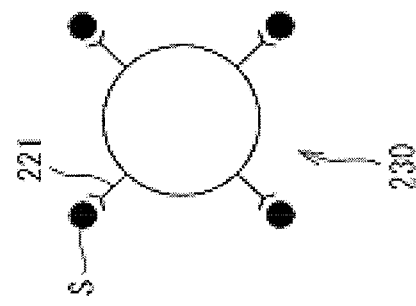
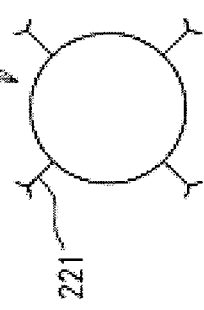
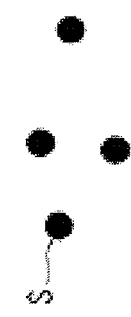
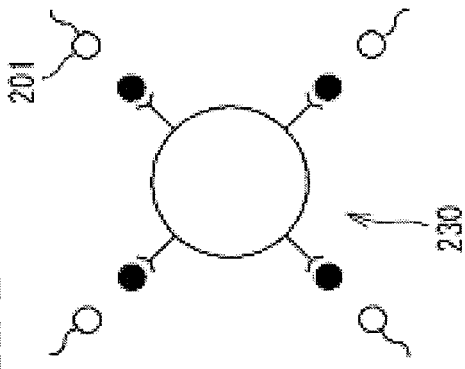
FIG. 22A  FIG. 22B  FIG. 22C  FIG. 22D

DETECTION DEVICE FOR DETECTING A TEST SUBSTANCE

FIELD OF THE INVENTION

The present invention relates to a detection device for detecting a test substance, an electrode substrate, a working electrode, an inspection tip, method of detecting a test substance, and a method of detecting a sample substance. More specifically, the present invention relates to a detection device for detecting a test substance used to detect or quantify a sample substance, and for clinical examination and diagnosis of disease using same, an electrode substrate, a working electrode, an inspection tip, method of detecting a test substance, and a method of detecting a sample substance.

BACKGROUND

Clinical examination and diagnosis of disease are accomplished by detecting disease-related genes and proteins contained in biological samples using methods such as gene detection, immunological detection and the like. It has been proposed that the electrical current produced by photoexcitation of a photochemically active labeled substance (photoelectrochemical detection methods) should be utilized in methods for the detection of sample substances such as proteins and gene detection methods in clinical examination and diagnosis of disease (for example, refer to U.S. Patent Publication No. 2009/0294305).

U.S. Patent Publication No. 2009/0294305 discloses a method using a test substance such as photochemically active sensitizing dye or the like to detect a sample substance based on the electrical current produced by photoexcitation of the test substance. In the method disclosed in U.S. Patent Publication No. 2009/0294305, a sample substance is labeled with a photochemically active test substance. Then, the labeled sample substance is irradiated with light to photoexcite the sensitizing dye contained in the labeled sample substance. The electrical current produced by the photoexcitation is then measured. The sample substance can be detected with high sensitivity based on the current measurement result. It is desirable to improve detection sensitivity to detect very small amounts of a sample substance.

SUMMARY OF THE INVENTION

The scope of the present invention is defined solely by the appended claims, and is not affected to any degree by the statements within this summary.

In view of this information, an object of the present invention is to provide a test substance detection device, electrode substrate, working electrode, inspection tip, and method of detecting a sample substance capable of detecting a test substance with high sensitivity.

A method which relatively increases the photocurrent originating in the test substance can be increased by increasing the intensity of excitation light emitted from the light source is known as a method that improves the sample substance detection sensitivity in photoelectrochemical detection methods. There is concern about adversely affecting the signal-to-noise (S/N) ratio due to a relative increase to the point a photocurrent does not originate in the test substance.

The present inventors have discovered that a photocurrent originating in the test substance can be increased without increasing the photocurrent that does not originate in the test substance by reflecting the excitation light that passes through the working electrode toward the test substance on the working electrode.

A first aspect of the present invention is a detection device which photoelectrochemically detects a test substance that releases electrons by photoexcitation, comprising:

an optically permeable working electrode body which accepts electrons from the test substance;

a counter electrode;

a light source which irradiates excitation light on the test substance on the working electrode body;

a reflective part which reflects the excitation light that is emitted from the light source and passes through the working electrode body, toward the test substance on the working electrode body.

A second aspect of the present invention is an electrode substrate which is used to photoelectrochemically detect a test substance that releases electrons by photoexcitation, comprising:

a substrate body;

an optically permeable working electrode body which is formed on the substrate body and accepts electrons from the test substance; and a reflective part which is formed on the substrate body and reflects the excitation light that is emitted from the light source and passes through the working electrode body, toward the test substance on the working electrode body.

A third aspect of the present invention is a working electrode which is used to photoelectrochemically detect a test substance that releases electrons by photoexcitation, comprising:

an optically permeable working electrode body which is formed on the substrate body and accepts electrons released from the test substance; and a reflective part which is formed on the substrate body and reflects the excitation light that is emitted from the light source and passes through the working electrode body, toward the test substance on the working electrode body.

A fourth aspect of the present invention is an inspection tip which photoelectrochemically detects a test substance that releases electrons by photoexcitation, comprising:

an electrode substrate comprising a substrate body, an optically permeable working electrode body which is formed on the substrate body and accepts electrons from the test substance, and a reflective part which is formed on the substrate body and reflects the excitation light that is emitted from the light source and passes through the working electrode body toward the test substance on the working electrode body, and a counter electrode.

A fifth aspect of the present invention is a method of detecting a test substance by photoelectrochemically detecting a test substance which releases electrons by photoexcitation using an optically permeable working electrode and a counter electrode, comprising the steps of:

establishing the test substance on the working electrode;

irradiating excitation light on the test substance on the working electrode;

reflecting the excitation light which passes through the working electrode toward the test substance on the working electrode; and measuring the electrical current flowing between the working electrode and the counter electrode.

A sixth aspect of the present invention is a method of detecting a sample substance by photoelectrochemically detecting the sample substance using an optically permeable working electrode and a counter electrode, comprising the steps of:

forming a composite body of sample substance and a labeled binder configured with the sample substance in contact with the labeled binder such that the sample substance is captured by the binding substance that is labeled with a labeling substance;

establishing the at least the labeled substance on the working electrode; irradiating excitation light on the labeled substance on the working electrode;

reflecting the excitation light which passes through the working electrode toward the labeled substance on the working electrode; and measuring the electrical current flowing between the working electrode and the counter electrode.

A test substance and a sample substance can be detected with high sensitivity according to the test substance detection device, electrode substrate, working electrode, inspection tip, and method of detecting a sample substance of the present invention.

BRIEF DESCRIPTION OF THE DRAWINGS

FIG. 20 briefly shows each process of the processing sequence of another embodiment of the method of detecting a test substance of the present invention;

FIG. 22 briefly shows the process of separation from the sample substance capture process in each process of the embodiment of the method of detecting a sample substance of the present invention;

DETAILED DESCRIPTION OF THE PREFERRED EMBODIMENTS

Figure 1:
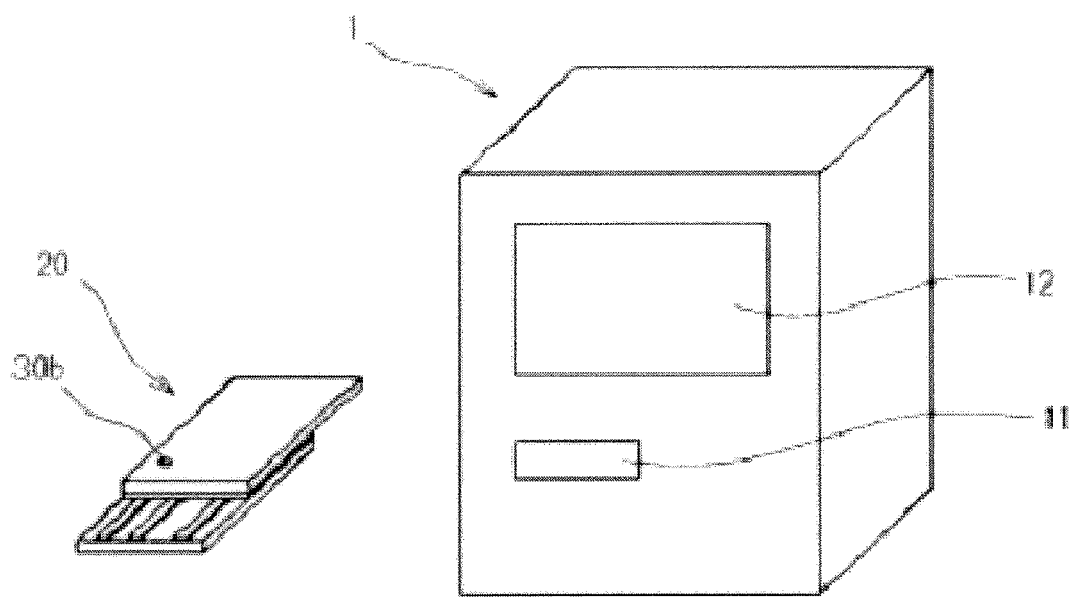
FIG. 1 is a perspective view showing the structure of an embodiment of the test substance detection device of the present invention.

The preferred embodiments of the present invention will be described hereinafter with reference to the drawings.

[Definition of Terms]

In the specification, "test substance that releases electrons by photoexcitation" is a substance targeted for photoelectrochemical detection on the working electrode, and includes a labeled substance. The labeled substance may be at least one substance selected from a group which includes a metal complexes, organic phosphors, quantum dots, and inorganic phosphors. Examples of the labeled substances include metal phthalocyanine, ruthenium, osmium complex, iron complex, zinc complex, 9-phenyl-xanthene dyes, cyanine dyes, cyanine metalloproteinases, xanthene dyes, triphenylmethane dyes, acridine dyes, oxazine dyes, coumarin dyes, merocyanine dyes, rhoda-cyanine dyes, polymethine dyes, porphyrin dyes, phthalocyanine dyes, rhodamine dyes, xanthene dyes, chlorophyll pigments, eosin dyes, mercurochrome dyes, indigo dyes, BODIPY dyes, CALFluor dyes, Oregon Green dyes, Rhodol Green, Texas Red, Cascade Blue, nucleic acids (DNA, RNA and the like), cadmium selenide, cadmium telluride, Ln2O3: Re, Ln2O2S: Re, ZnO, CaWO4, $MO.xAl_{2O3}:_{Eu}$, $Zn2SiO4$: Mn, LaPO4: Ce, Tb, Cy3, Cy3.5, Cy5, Cy5.5, Cy7, Cy9 and Cy7.5 (both manufactured by Amersham Biosciences); Alexa Fluor 355, Alexa Fluor 405, Alexa Fluor 430, Alexa Fluor 488, Alexa Fluor 532, Alexa Fluor 546, Alexa Fluor 555, Alexa Fluor 568, Alexa Fluor 594, Alexa Fluor 633, Alexa Fluor 647, Alexa Fluor 660, Alexa Fluor 680, Alexa Fluor 700, Alexa Fluor 790 and Alexa Fluor 750 (both manufactured by Molecular Probes); DY-610, DY-615, DY-630, DY-631, DY-633, DY-635, DY-636, EVOblue10, EVOblue30, DY-647, DY-650, DY-651, DY-800, DYQ-DYQ 660- and 661 (both manufactured by Dyomics); Atto425, Atto465, Atto488, Atto 495, Atto520, Atto532, Atto550, Atto565, Atto590, Atto594, Atto610, Atto611X, Atto620, Atto633, Atto635, Atto637, Atto647, Atto655, Atto680, Atto700, Atto740 and Atto725 (both, Atto-manufactured by TEC GmbH); VivoTagS680, VivoTagS750 and VivoTag680 (both manufactured by VisEnMedical) and the like. Note that Ln represents La, Gd, Lu, or Y, Re represents a lanthanide element, M represents an alkaline earth metal element, and x represents an integer from 0.5 to 1.5. For other examples of labeled substances refer to U.S. Patent Publication No. 2009/0294305, U.S. Patent Publication No. 5893999, and Japanese Patent Publication No. 2008-154179.

In the specifications, the test substance also may be a composite material in which the labeled substance is directly bonded to the sample substance. The test substance also may be a composite material in which, after the sample substance is captured in a solid phase, the labeled substance is bonded to a substance that is present according to the amount of captured sample substance. In this case, solid phase pertains to, for example, a substrate formed of silicon dioxide (glass), metals and other inorganic materials, a plastic substrate of polyethylene terephthalate, polyimide, or a substrate including at least one thereof; fibers; membrane; nanostructures (for example, silica-based nanostructures such as mesoporous silica, porous alumina, and the like); and particles such as glass beads, magnetic beads, metal particles, plastic particles such as beads, or particles containing at least one thereof.

In the specifications, "modified substance used as an attractant" pertains to a substance which attracts the test substance and labeled substance to the vicinity of the working electrode.

[Structure of the detection Device]

An example of the test substance detection device of the present invention is described hereinafter with reference to the accompanying drawing.

FIG. 1 is a perspective view showing an embodiment of the test substance detection device of the present invention. The detection device 1 is a detection device used for photoelectrochemical detection of a test substance that releases electrons by photoexcitation.

The detection device 1 is provided with a tip receiver 11 for inserting the inspection tip 20, and a display 12 for displaying the detection result.

Figure 2:
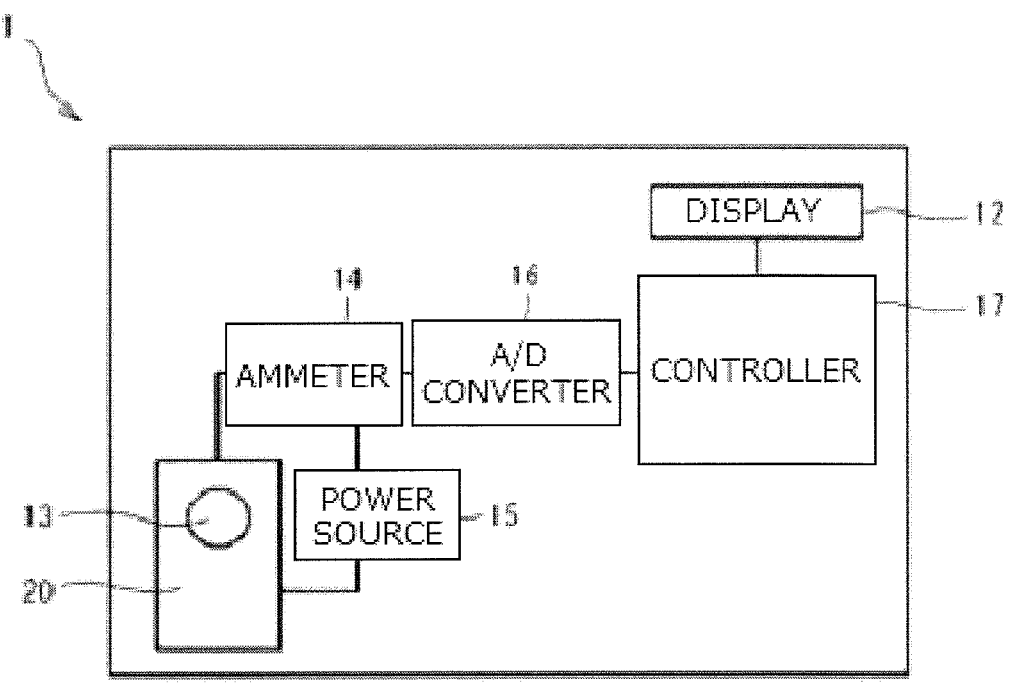
FIG. 2 is a block diagram showing the structure of the detection device in FIG. 1.

FIG. 2 is a block diagram showing the structure of the detection device 1 in FIG. 1. The detection device 1 is provided with a display 12, light source 13, ammeter (current measuring part) 14, power source (electric potential application part) 15, A/D converter 16, and controller 17.

The light source 13 emits light which irradiates the test substance present on the working electrode of the inspection tip 20 to excite the test substance. The light source 13 also may be disposed on the electron acceptor surface side of the working electrode of the inspection tip 20 (described layer). The light source 13 also may be disposed on the side opposite from the electron acceptor surface of the working electrode of the inspection tip 20 (described later). The light source 13 may be a light source which generates excitation light. Fluorescent light, black light, germicidal lamp, incandescent lamp, low pressure mercury lamp, high pressure mercury lamp, xenon lamp, mercury-xenon lamp, halogen lamp, metal halide lamp, LED (white LED, blue LED, green LED, red LED and the like), laser light (carbon dioxide gas laser, dye laser, semiconductor laser), sunlight and the like may be used as the light source. Among these light sources, fluorescent lamp, incandescent lamp, xenon lamp, halogen lamp, metal halide lamp, LED, laser, or sunlight are preferable. Among these light sources, lasers are most preferable. The light source also may emit only light of a specific wavelength band via a splitter and bandpass filter as necessary.

The ammeter 14 measures the current flowing within the inspection tip 10 originating from the electrons released from the excited test substance.

The power source 15 supplies a predetermined potential to the electrode provided on the inspection tip 20.

The A/D converter 16 performs digital conversion of the photoelectric current value measured by the ammeter 14.

The controller 17 is configured by a CPU, RAM, ROM and the like, and controls the operation of the display 12, light source 13, ammeter 14, and power source 15. The controller 17 estimates the amount of test substance from the photoelectric current value obtained from the digital conversion by the A/D converter 17 based on the previously prepared calibration curve showing the relationship between amount of test substance and the photoelectric current.

The display 12 then displays the amount of test substance estimated by the controller 17.

Figure 3:
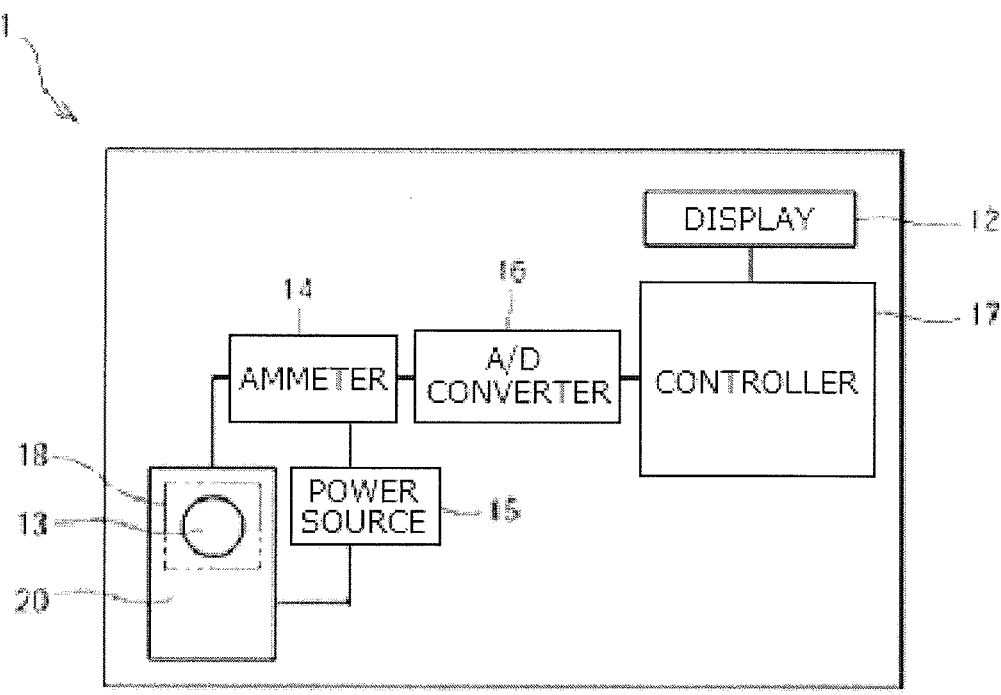
FIG. 3 is a block diagram showing the structure of another embodiment of the test substance detection device of the present invention.

Note that in the detection device 1 a reflective part 18 (refer to FIG. 3) may be positioned to face the light source 13 through the inspection tip 20 when using an inspection tip which does not have a reflective layer as the reflective part in the inspection tip. The reflective part 18 is configured of a material capable of reflecting the excitation light. Such materials include but are not limited to, for example, metals such as platinum, aluminum, gold, silver, copper, alloys, and metal compounds.

Figure 4:
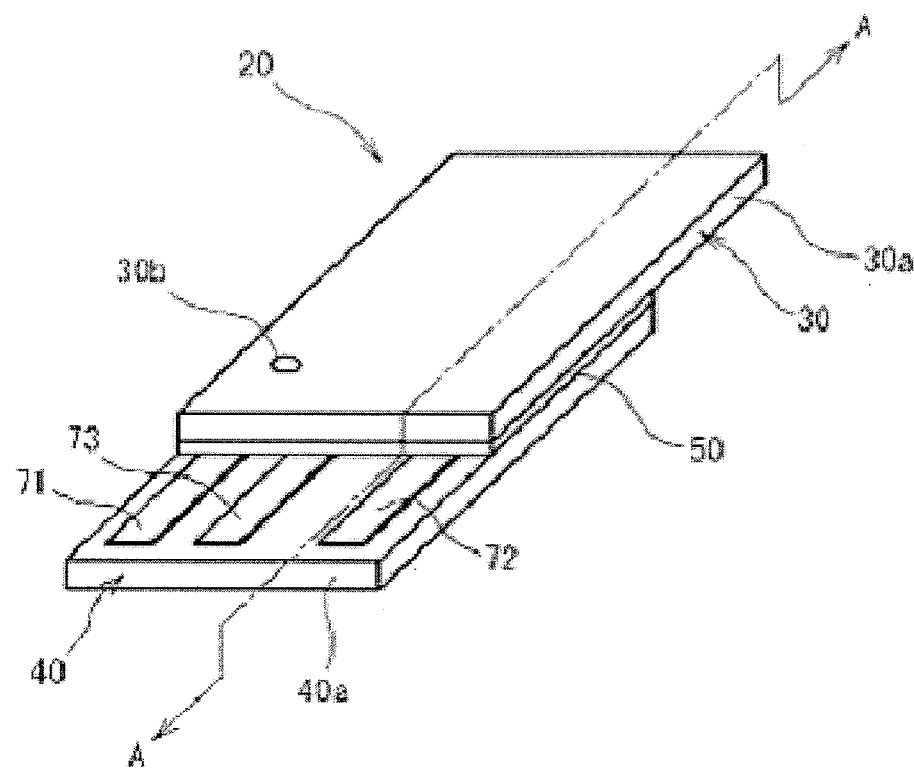
FIG. 4 is a perspective view showing the an embodiment of the inspection tip of the present invention.
Figure 5:
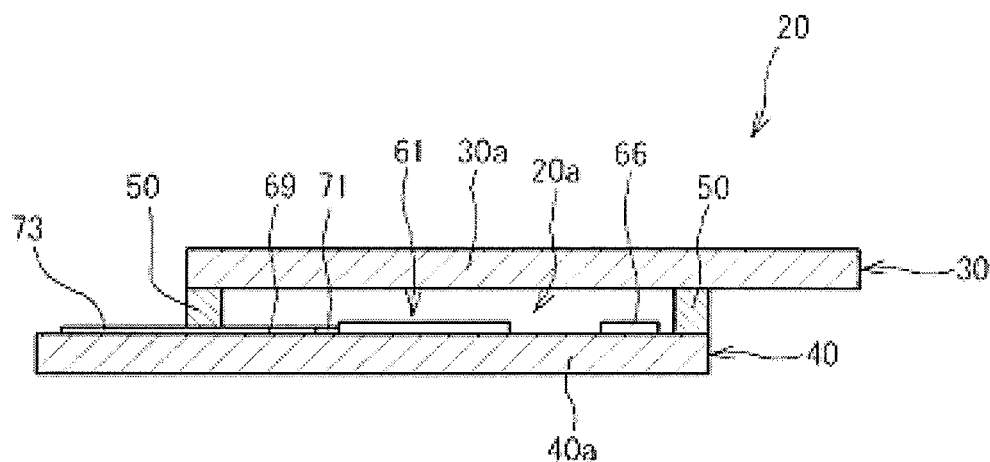
FIG. 5 is a cross sectional view on the A-A line of the inspection tip in FIG. 4.

The structure of an embodiment of the inspection tip of the present invention is described below. FIG. 4 is a perspective view showing an embodiment of the inspection tip 20 of the present invention; FIG. 5 is a cross sectional view on the A-A line of the inspection tip 20 in FIG. 4;

The inspection tip 20 is provided with a top substrate 30, a bottom substrate 40 which is disposed below the top substrate 30, and an interval holding member 50 which is interposed between the top substrate 30 and the bottom substrate 40. In the inspection tip 20, the top substrate 30 and the bottom substrate 40 are arranged so as to overlap on one side. The interval holding member 50 is interposed at the overlapping part of the top substrate 30 and the bottom substrate 40.

Figure 6A:
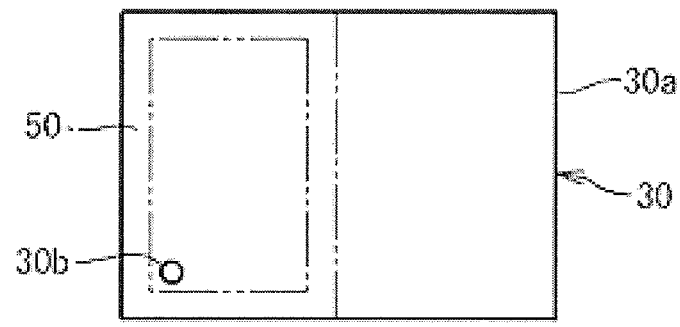
FIG. 6A is a top view of the top substrate included in the inspection tip in FIG. 4.

The top substrate 30 is configured by a substrate main body 30a as shown in FIG. 6A. The substrate main body 30a has a sample injection inlet 30b for injecting a sample containing the test substance into the interior. The sample injection inlet 30b is on the inner side of the substrate main body 30a from the part where the interval holding member 50 is interposed.

The substrate main body 30a is formed in a rectangular shape. Note that the shape of the substrate main body 30a is not specifically limited and also may be polygonal-shaped, disk-shaped or the like. From the perspective of ease of fabrication and handling of the substrate, a rectangular shape is preferable. The material constituting the substrate main body 30a is not specifically limited, and may be, for example, glass, plastics such as polyethylene terephthalate, polyimide resins, and inorganic materials such as metals. Among these materials, glass is preferable from the perspectives of optical transparency, adequate heat resistance, ensuring smoothness, and material cost reduction. From the perspective of ensuring sufficient durability, the thickness of the substrate main body 30a is preferably 0.01 to 1 mm, more preferably 0.1 to 0.7 mm, and most preferably about 0.5 mm. In addition, the size of the board body 30a is not specifically limited, but is usually about 20×20 mm depending on the number of items to be detected when detecting a wide variety of test substances and sample substances (many items).

Figure 6B:
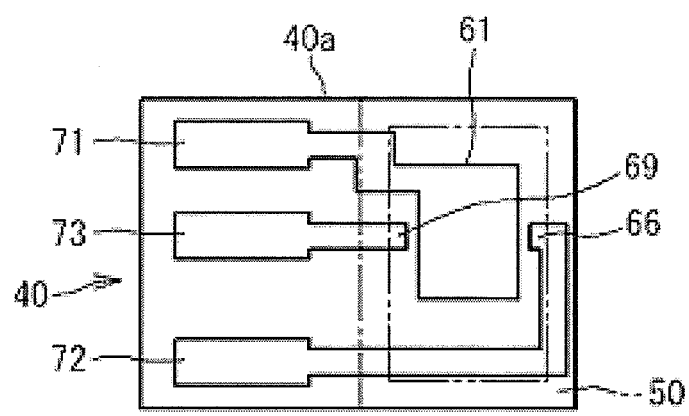
FIG. 6B is a top view of the bottom substrate included in the inspection tip in FIG. 4.

The bottom substrate 40 has a substrate main body 40a, working electrode 61, counter electrode 66, and reference electrode 69 as shown in FIG. 6B. The substrate main body 40a has substantially the same shape and dimensions as the substrate main body 30a of the top substrate 30. The surface of the substrate main body 40a has a working electrode 61, an electrode lead 71 which is connected to the working electrode 61, a counter electrode 66, an lead electrode 72 which is connected to the counter electrode 66, a reference electrode 69, and an electrode lead 73 which is connected to the reference electrode 69.

The material constituting the substrate main body 40a is not specifically limited, and may be, for example, glass, plastics such as polyethylene terephthalate, polyimide resins, and inorganic materials such as metals. Among these materials, glass is preferable from the perspectives of sufficient optical transparency, adequate heat resistance, ensuring smoothness, and material cost reduction.

The material, thickness, and size of the substrate main body 40a is identical to the material, thickness, and size of the substrate main body 30a of the top substrate 30.

The working electrode 61 is approximately square in shape. The working electrode 61 is disposed on one side (right side in FIG. 6B) of the substrate main body 40a. The electrode lead 71 extends from the working electrode 61 toward the other side (left side in FIG. 6B) of the substrate main body 40a. The counter electrode 66 is disposed on the outer side from the working electrode 61 (right side of the working electrode 61 in FIG. 6B). The electrode lead 72 extends from the counter electrode 66 toward the other side (left side in FIG. 6B) of the substrate main body 40a and detours around the working electrode 61. The reference electrode 69 is positioned facing the counter electrode 66 with the working electrode 61 interposed therebetween. The electrode lead 73 extends from the reference electrode 69 toward the other side (left side in FIG. 6B) of the substrate main body 40a. The electrode lead 71 of the working electrode 61, the electrode lead 72 of the counter electrode 66, and the electrode lead 73 of the reference electrode 69 are arranged so as to be mutually parallel at the other end of the substrate main body 40a.

Figure 7A:
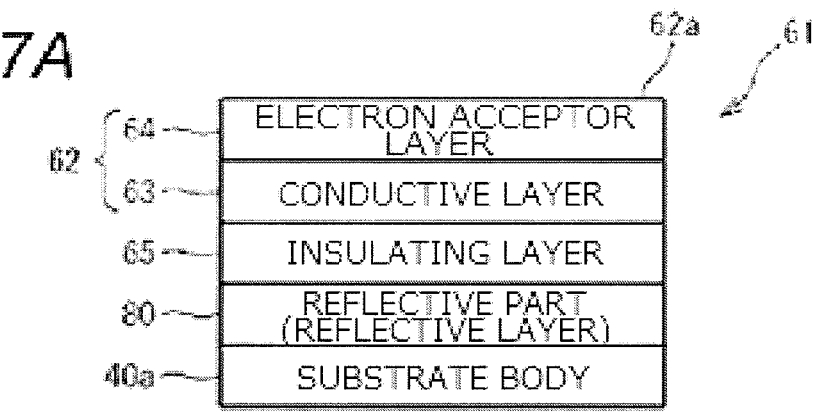
FIG. 7A is a brief plan view showing the part including the working electrode of the inspection tip in FIG. 4.

The working electrode 61 is configured by a working electrode body 62, an insulating layer 65, and a reflective layer 80 as shown in FIG. 7A. The working electrode 61 has the reflective layer 80 as a reflective part, the insulating layer 65, and the working electrode body 62 sequentially formed on the surface of the substrate main body 40a.

The working electrode body 62 is configured by a conductive layer 63, and an electron receptor layer 64 formed on the surface of the conductive layer 63.

The conductive layer 63 is formed of a conductive material (hereinafter referred to as "working electrode material (A)") which transmits excitation light. Working electrode material (A) includes, for example, materials exhibiting optical transparency and electrical conductivity and may contain atoms of group 12 elements, group 14 elements, or group 13 elements of the periodic table of the elements. These materials may include, but are not limited to, zinc oxide, zinc oxide-based materials such as zinc oxide containing boron as a dopant, zinc oxide containing aluminum as a dopant, zinc oxide containing gallium as a dopant, zinc oxide containing indium as a dopant, indium oxide, indium oxide-based materials such as indium oxide containing tin a dopant; tin oxide, tin oxide-based materials such as tin oxide containing antimony as a dopant (ATO), tin oxide contained fluorine as a dopant (FTO), titanium oxide-based materials such as titanium oxide containing tantalum as a dopant, titanium oxide containing niobium as dopant. The thickness of the conductive layer 63 is preferably 1 to 1,000 nm, and more preferably 10 to 200 nm.

Note that insofar as the conductive layer 63 is conductive and optically transparent, the conductive layer 63 may be a composite substrate that has a conductive layer composed of a conductive material formed on the surface of a non-conductive substrate composed of a non-conductive material that is optically transparent, such as glass, plastic and the like. The shape of the conductive layer may be either a thin film or a spot. In this case, the thickness of the working electrode 61 is preferably 1 to 1,000 nm, and more preferably 10 to 200 nm. The conductive material configuring the conductive layer may be, for example, indium oxide containing a tin dopant, tin oxide containing a fluorine dopant, tin oxide containing a antimony dopant, zinc oxide containing a gallium dopant, zinc oxide containing an aluminum dopant. Among these materials, tin oxide containing fluorine and indium oxide containing tin are preferable.

The conductive layer 63 may be formed by, for example, a film formation method according to the type of material configuring the conductive layer 63. Deposition method, sputtering, imprinting, screen printing method, plating method, sol-gel method, spin coating, dipping, vapor deposition and the like may be used as a film forming method.

The electron acceptor layer 64 is optically transparent. The electron acceptor layer 64 contains a substance capable of accepting electrons (electron acceptor material). The electron acceptor material may be a material capable of producing an energy level by electron injection from a photoexcited labeled substance (described later). In this case, "energy level by electron injection from a photoexcited labeled substance" means a conduction band when, for example, a semiconductor is used as the electron acceptor layer. That is, the electron acceptor material may have a lower energy level than the lowest unoccupied molecular orbital (LUMO) of the labeled substance (described later). energy level The electron acceptor substance may be, but is not limited to, for example, indium oxide, indium oxide-based materials such as indium oxide containing a tin dopant; tin oxide, tin oxide-based materials such as tin oxide containing a antimony dopant (ATO), tin oxide containing a fluorine dopant (FTO) and the like. Among these materials, tin oxide containing fluorine as a dopant or indium oxide containing tin as a dopant has the properties to function as a conductive substrate as well as the electron acceptor substance. Thus, using these materials provides the functionality of the working electrode via just an electron acceptor layer without using a conductive substrate. Note that when the conductive layer 63 is a composite substrate, the electron acceptor layer 64 is formed on the conductive substrate. The thickness of the electron acceptor layer 64 is usually 0.1 to 100 nm, and preferably 0.1 to 10 nm. The electron acceptor layer 64 may be formed by a method similar to the method used to form the conductive layer 63 depending on the type of material used to configure the electron acceptor layer 64.

The insulating layer 65 is configured by an insulating material. The insulating material is not specifically limited insofar as such material is transparent. For example, glass, silicon dioxide ($SiO_2$), synthetic resin such as fluoride resins, plastics and the like may be used. The insulating layer 65 may be formed by a suitable method according to the type of insulating material. These methods include, for example, sputtering, vapor deposition, screen printing method, spin coating, imprinting, spray coating and the like.

The reflective layer 80 is configured by material capable of reflecting the excitation light. Such materials include but are not limited to, for example, metals such as platinum, aluminum, gold, silver, copper, alloys, and metal compounds. The reflective layer 80 may also be the same shape and size as the working electrode body 62. The reflective layer 80 may also reflect the excitation light transmitted through the working electrode body 62. Therefore, the size of the reflective layer 80 may also be the same size or larger than the irradiation position on the working electrode body 62. The reflective layer 80 may be formed by, for example, sputtering, vapor deposition, screen printing, plating treatment, imprinting, spin coating and the like. The surface of the reflective layer 80 is preferably smooth from the perspective of efficient reflection of the excitation light transmitted through the working electrode body 62.

Figure 7B:
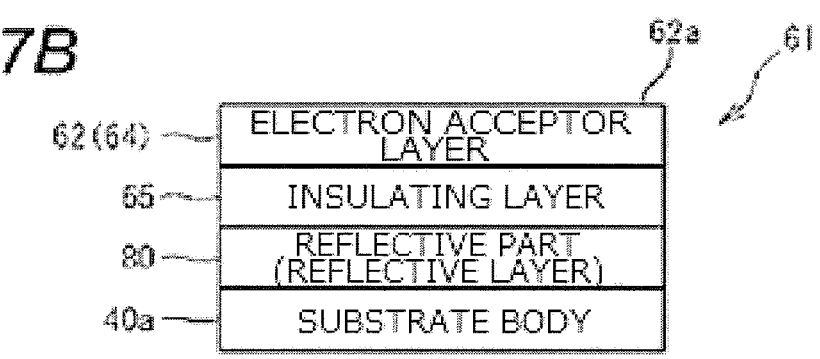
FIG. 7B is a brief plan view showing a modification of the part including the working electrode of the inspection tip in FIG. 4.

Note that, in the present invention, the working electrode 61 may be configured by the electron acceptor layer 64, insulating layer 65, and reflective layer 80 as shown in FIG. 7B. In this case, in the working electrode 61, the reflective layer 80, insulating layer 65, and electron acceptor layer 64 are sequentially formed on the surface of the substrate body 40a.

Although the working electrode 61 of the present embodiment is provided with a reflective layer on the surface of the substrate body 40a, the present invention is not limited to this arrangement inasmuch as the substrate body 40 also may serve as the reflective layer as shown in FIG. 7B. At such time, an inorganic material such as, for example, a metal, may be used as the material of the substrate body 40a.

The working electrode 61 is subjected to surface treatment using a silane coupling agent or the like. The surface of the working electrode 61 can be suitably adjusted to be hydrophilic or hydrophobic via this surface treatment. Cationic silane coupling agents such as, for example, aminopropyl triethoxysilane (APTES) and the like, may be used as the silane coupling agent.

A capture substance may be fixed on the electron acceptor surface 62a of the working electrode body 62 of the working electrode 61. The capture substance may be any substance that can capture the test substance. Capture substances include, for example, nucleic acids, proteins, peptides, oligosaccharides, antibodies, and nanostructures with specific recognition ability. The capture substance may be suitably selected according to the type of test substance. The amount of capture substance on the electron acceptor surface 62a may be suitably set according to purpose and use. Fixing the capture substance on the electron acceptor surface 62a may be accomplished via a linkage group that chemically adheres to the working electrode body 62. Usable linking groups may include, for example, a thiol group, hydroxyl group, a phosphate group, a carboxyl group, carbonyl group, aldehyde, sulfonic acid, an amino group and the like. The capture substance also may be fixed by physical adhesion and methods using photoset resin.

The counter electrode 66 is a metal layer composed of a conductive material. The conductive material may be, for example, gold, silver, copper, carbon, platinum, palladium, chromium, aluminum, alloys thereof containing at least one or these metals such as nickel, indium-tin oxide, indium oxide, metal oxides such as ATO and FTO, titanium, titanium oxide, and titanium compounds such as titanium nitride. The thickness of the metal layer is preferably 1 to 1,000 nm, and more preferably 10 to 200 nm.

The reference electrode 69 is a metal layer composed of a conductive material. The conductive material may be, for example, gold, silver, copper, carbon, platinum, palladium, chromium, aluminum, alloys thereof containing at least one or these metals such as nickel, indium-tin oxide, indium oxide, metal oxides such as ATO and FTO, titanium, titanium oxide, and titanium compounds such as titanium nitride. The thickness of the metal layer is preferably 1 to 1,000 nm, and more preferably 10 to 200 nm. Note that although the reference electrode 69 is provided in the present embodiment, the reference electrode 69 need not necessarily be provided in the present invention. Depending on the type and thickness of the electrode used in the counter electrode 66, the counter electrode 66 may serve as the reference electrode 69 when measuring a current that has a very slight influence on a voltage drop (for example, 1 µA or less). On the other hand, when measuring a large current, the reference electrode 69 is preferable from the perspective of suppressing the voltage drop influence and stabilizing the voltage supplied to the working electrode 61.

Interval holding member 50 is formed in the shape of a rectangular ring, which is made of silicone rubber insulators. The interval holding member 50 is arranged so as to circumscribe a region in which the working electrode 61, counter electrode 66 and reference electrode 69 are mutually facing (refer to FIGS. 5 and 6). A gap is formed between the top substrate 30 and the bottom substrate 40, and the gap is equivalent to the thickness of the interval holding member 50. Hence, a space 20a is formed between the electrodes 61, 66, and 69 to accommodate a sample and electrolyte. The thickness of the interval holding member 50 is usually 0.2 to 300 µm. In the present invention, the material constituting the interval holding member 50 may be, for example, a double-sided tape of polyester film rather than silicone rubber.

[Detection Device and Inspection Tip Modifications]

Figure 8:
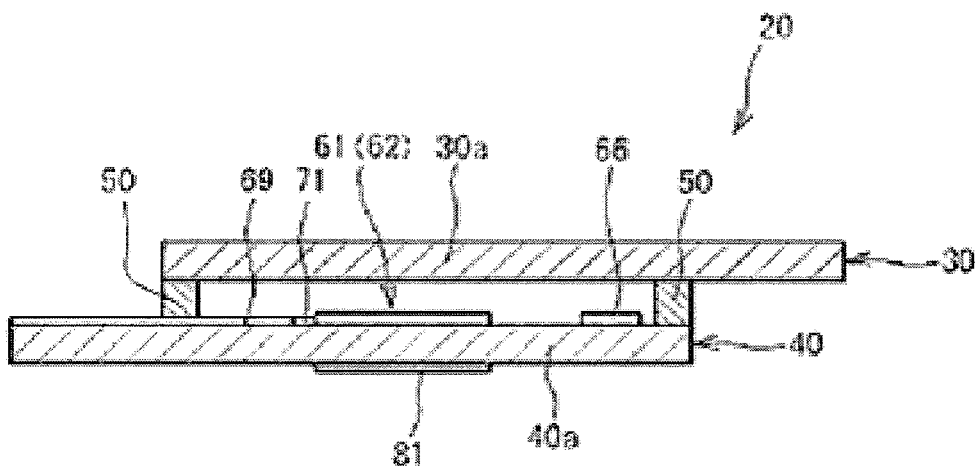
FIG. 8 is a cross sectional view of another embodiment of the inspection tip of the present invention.
Figure 9A:
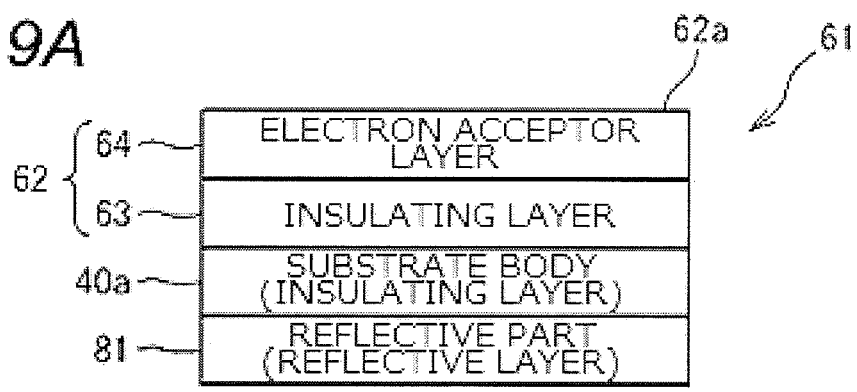
FIG. 9A is a brief plan view showing the part including the working electrode of the inspection tip in FIG. 8.
Figure 9B:
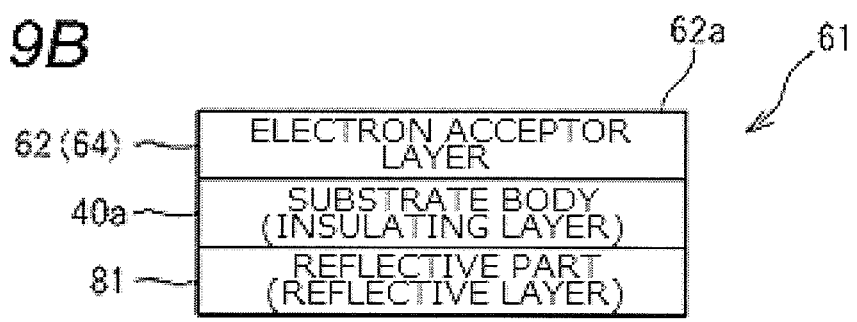
FIG. 9B is a brief plan view showing a modification of the part including the working electrode of the inspection tip in FIG. 8.

Note that in the present invention the reflective part may be provided at a position separated from the working electrode body in the detection device. Specifically, for example, a reflective layer 81 which acts as a reflective part may be disposed on the opposite side from the surface on which the working electrode 61 is formed in the substrate body 40*a*, as shown in FIG. 8. In this case, the reflective layer 81 is formed as an insulating layer on one side of the substrate body 40*a*, and the conductive layer 63 and the electron acceptor layer 64 are sequentially formed on the other surface of the substrate body 40*a* as shown in FIG. 9A. Further, the reflective layer 81 may formed as an insulating layer on one side of the substrate body 40*a*, and the electron acceptor layer 64 may formed on the other surface of the substrate body 40*a* as shown in FIG. 9B. Note that in the structures of FIGS. 9(*a*) and 9(*b*) a transparent insulating material such as glass, plastic and the like may be used as the substrate body 40*a*.

Figure 10A:
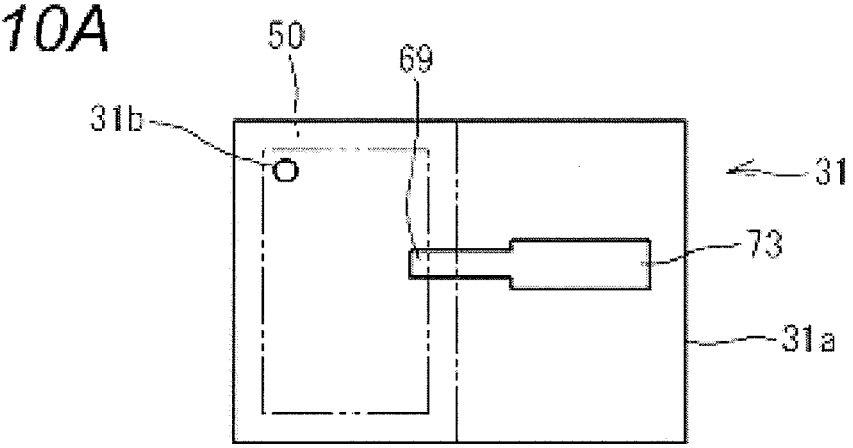
FIG. 10A is a plan view of a modification of the top substrate.
Figure 10B:
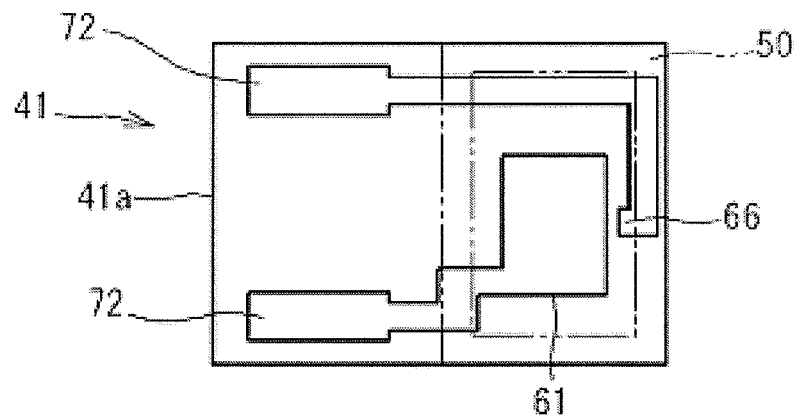
FIG. 10B is a plan view of a modification of the bottom substrate.
Figure 11A:
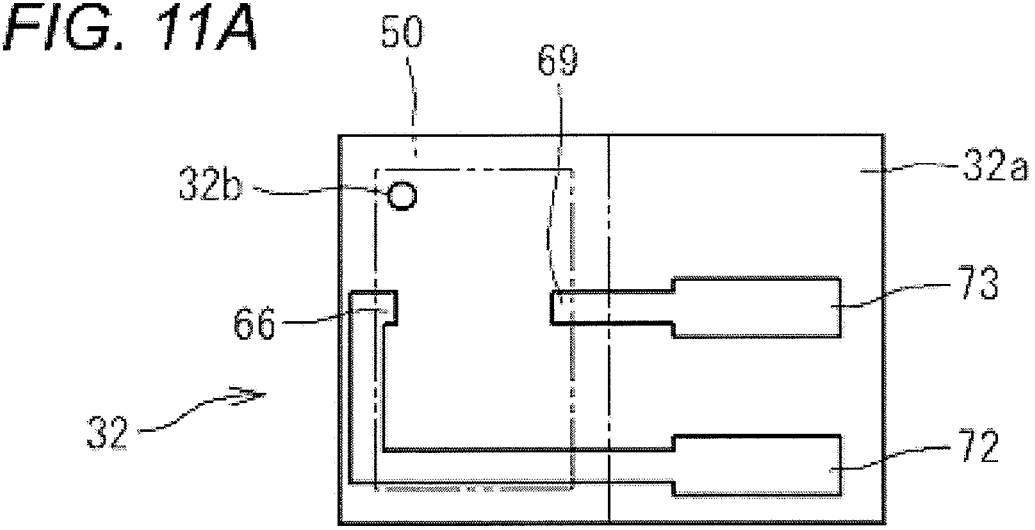
FIG. 11A is a plan view of a modification of the top substrate.
Figure 11B:
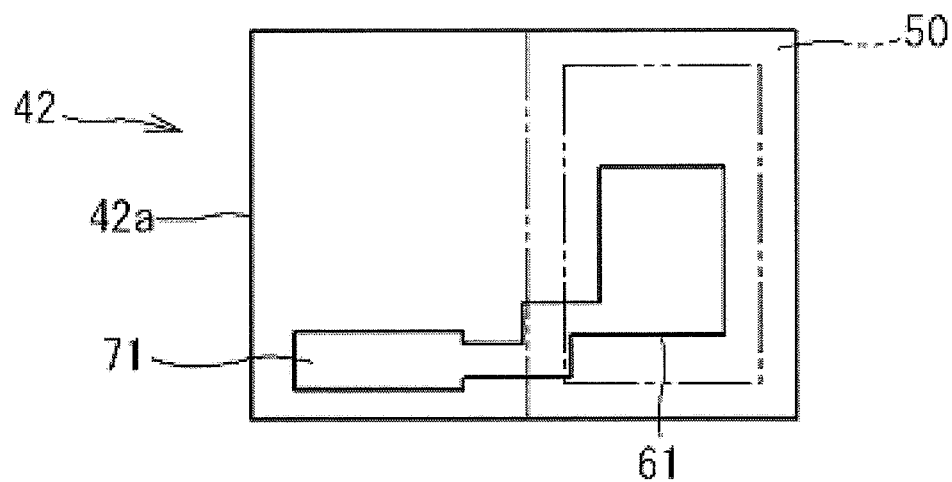
FIG. 11B is a plan view of a modification of the bottom substrate.

In the present invention, the working electrode 61, counter electrode 66, and reference electrode 69 may be disposed with the frame of the interval holding member 50 so that no electrode comes into contact with another electrode. Therefore, the working electrode 61, counter 66, and reference electrode 69 may be formed on different substrate bodies. That is, the inspection tip may have a top substrate 31 (refer to FIG. 10A wherein a sample injection inlet 31*b* and reference electrode 73 are formed on a substrate body 31*a*, and a bottom substrate 41 (refer to FIG. 10B wherein the working electrode 61 and counter electrode 66 are formed on the substrate body 41*a*. Further, the inspection tip may have a top substrate 32 (refer to FIG. 11A wherein a sample injection inlet 32*b*, counter electrode 66, and reference electrode 69 are formed on a substrate body 32*a*, and a bottom substrate 42 (refer to FIG. 11B wherein the working electrode 61 is formed on the substrate body 42*a*.

Figure 12A:
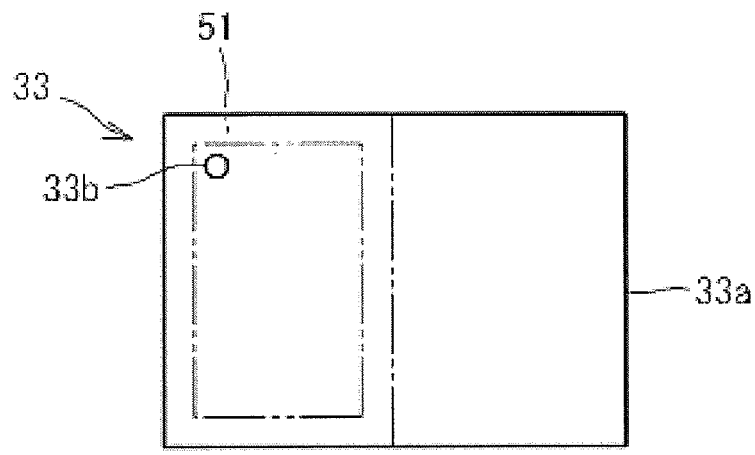
FIG. 12A is a plan view of a modification of the top substrate.
Figure 12B:
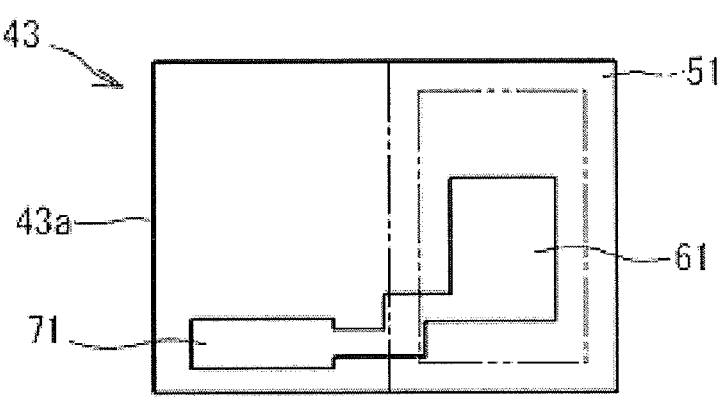
FIG. 12B is a plan view of a modification of the bottom substrate.
Figure 12C:
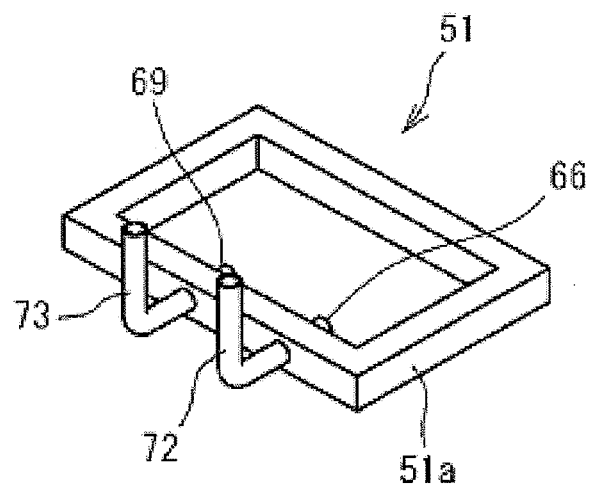
FIG. 12C is a perspective view of a modification of the interval holding member.

In the present invention, the counter electrode 66 and the reference electrode 69 need not be thin film electrodes formed on a substrate body. That is, the inspection tip may have a top substrate 33 (refer to FIG. 12A wherein a sample injection inlet 33*b* is formed on a substrate body 33*a*, a bottom substrate 43 (refer to FIG. 12B wherein the working electrode 61 is formed on the substrate body 43*a*, and an interval holding member 51 wherein the counter electrode 66 and the reference electrode 69 are provided on a member body 51*a*. In this case, at least either the counter electrode 66 or the reference electrode 69 is provided on the member body of the interval holding member. The other electrodes, except those electrodes provided on the member body, may be provided on either the top substrate and bottom substrate.

In the present invention, the insulating layer 65 may also function as a substrate body. In this case, it is possible to omit the substrate body.

[Method of Detecting a Test Substance]

The method of detecting a test substance of the present invention is a method of detecting a test substance by photo-electrochemically detecting a test substance which releases electrons by photoexcitation using an optically permeable working electrode and a counter electrode, comprising:

(1-1) a step of establishing the test substance on the working electrode body;

(1-2) a step of irradiating excitation light on the test substance on the working electrode body;

(1-3) a step of reflecting the excitation light transmitted through the working electrode body toward the test substance on the working electrode body; and (1-4) a step of measuring the electrical current flowing between the working electrode body and the counter electrode. Although the detection device and inspection tip described above are used in method 1, the present invention is not limited to this usage.

One important aspect of method 1 is that the excitation light transmitted through the working electrode body is reflected toward the test substance on the working electrode body.

Usually, there is a marked increase in noise that accompanies signal increase when the photoexcitation intensity is increased without reflecting the excitation light transmitted through the working electrode body. Therefore, the detection sensitivity is greatly reduced.

In method 1 in which the transmitted excitation light is reflected, however, the signal can be unexpectedly increased while suppressing an increase in noise compared to when the excitation light transmitted through the working electrode body is not reflected. Hence, greater detection sensitivity is ensured by method 1.

Method 1 is classified into method 1-1 and method 1-2 below according to the type of procedure performed in step (1-1). Method 1-1 is a method which uses a capture substance to capture the test substance (refer to FIGS. 13 and 14). Method 1-2 is a method which attracts the test substance to the working electrode body (refer to FIGS. 19 and 20).

Figure 13:
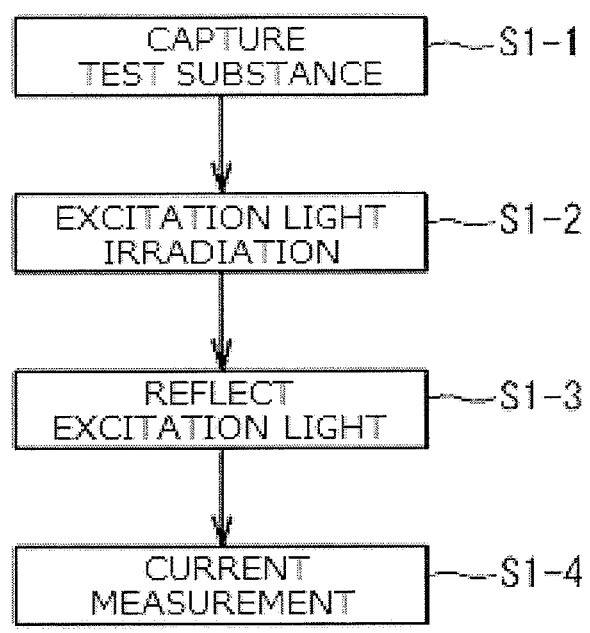
FIG. 13 is a flow chart showing the processing sequence of an embodiment of the method of detecting a test substance of the present invention.
Figure 14A:
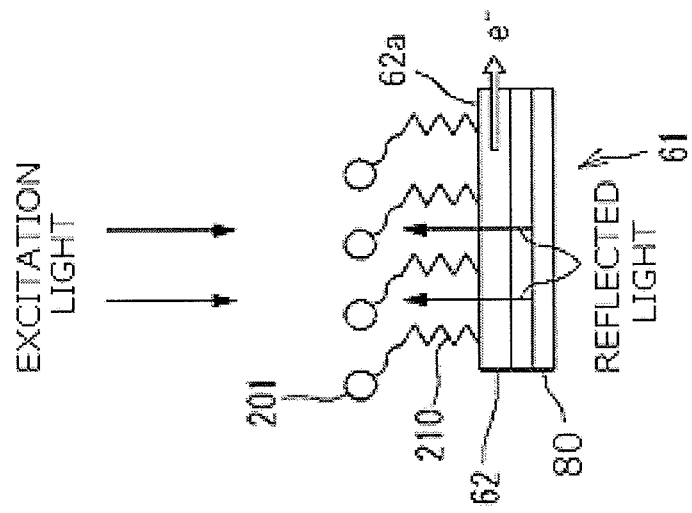
FIG. 14 briefly shows each process of the embodiment of the method of detecting a test substance of the present invention.
Figure 14B:
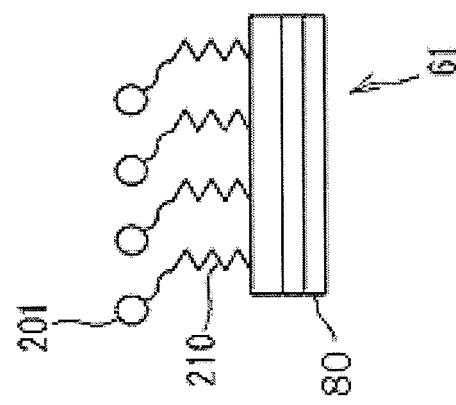
Figure 14C:
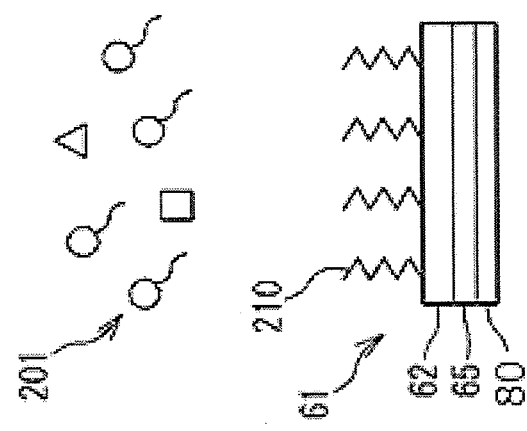

The method 1-1 is first described below referring to the drawings. FIG. 13 is a flow chart showing the processing sequence of an embodiment of the method of detecting a test substance of the present invention. FIG. 14 briefly shows each process of the embodiment of the method of detecting a test substance of the present invention. In the example below, a test substance is detected by the detection device 1 using the previously described inspection tip 20.

In method 1-1, the user first injects a liquid sample containing a test substance from the sample injection inlet 30*b* of the inspection tip 20. In this way the test substance 201 comes into contact with the working electrode body 62 on which the capture substance 210 is fixed. The test substance 201 is then captured by the capture substance 210 on the working electrode body 62 (refer to FIGS. 14A and 14B, and "test substance capture process" (step S1-1) in FIG. 13; equivalent to step (1-1)). In this step the test substance 201 is established on the working electrode body 62.

In step S1-1, capturing the test substance is accomplished under conditions that bind the capture substance 210 and the test substance 201. These conditions may be suitably selected according to the type of test substance 201. For example, when the test substance 201 contains nucleic acid, capturing the test substance 201 with the capture substance 210 can be accomplished in the presence of a solution such as phosphate buffered physiological saline solution.

The capture substance 210 may be suitably selected according to the type of test substance 201. For example, when the test substance 201 contains nucleic acid, the capture substance 210 may be an antibody of nucleic acid or a nucleic acid probe that hybridizes such nucleic acid. When the test substance 201 contains a protein or peptide, the capture substance 210 may be an antibody of the protein or peptide, a ligand of the protein, or a receptor protein of the peptide.

Although the test substance 201 is captured by the capture substance 210 which binds the test substance 201 in step S1-1, the present invention is not limited to this form of capture inasmuch as a complex of the capture substance 210 and a sample substance may be modified after the sample substance has been captured by the capture substance 210.

In step S1-1, the user washes the working electrode 61 as necessary. In this way material (contaminants) other than the test substance 201 can be eliminated. Washing can be accomplished by techniques according to the type of capture substance 210 and test substance 201. For example, when the either the test substance 201 or the capture substance 210 contains nucleic acid, a solution containing a surfactant and SSC (1×SSC composition: 0.15 M sodium chloride, 0.015 M sodium citrate, pH 7.0) may be used a the washing liquid. In this case, the washing liquid can remove the contaminants at high efficiency with a higher the concentration of the surfactant and lower concentration of SSC.

After step S1-1, the user then sets the inspection tip 20 in the chip receiver 11 of the detection device 1. The user then starts the operation of the detection device 1. At this time, excitation light is irradiated toward the test substance 201 on the working electrode body 62 by the light source 13 of the detection device 1 (refer to "excitation light" in FIG. 14C and "photoexcitation irradiation step (step S1-2)"; corresponds to step (S1-2)). The excitation light transmitted through the working electrode body 62 is reflected toward the test substance 201 on the working electrode body 62 by the reflective layer 80 of the working electrode 61 (refer to "reflected light" in FIG. 14C and "photoexcitation reflection step (step S1-3)" in FIG. 13; corresponds to step (1-3)). Thereafter, the photocurrent produced by the photoexcitation of the test substance 201 is measured by the ammeter 14 (refer to the "current measuring step" (S1-4) in FIG. 13; corresponds to step (1-4)).

Steps S1-2 through S1-4 are carried out in the presence of an electrolyte. Note that in the specification the series of processes in steps S1-2 through S1-4 are described separately for convenience. However, in practice, these steps 1-2 through 1-4 are performed substantially simultaneously.

A solution containing an electrolyte consisting of a salt capable of supplying electrons to the labeled substance in an oxidized state, aprotic polar solvent, protic polar solvent or a mixture of a protic polar solvent and aprotic polar solvent may be used as the electrolyte. The electrolyte also may contain other ingredients. Examples of materials useful as the electrolyte include iodide, bromide, metal complexes, thiosulfate, sulfite, and mixtures thereof. Examples of the electrolyte include metal iodides such as lithium iodide, sodium iodide, potassium iodide, cesium iodide, and calcium iodide; iodized salts of quaternary ammonium compounds such as tetraalkylammonium iodide, pyridinium iodide, imidazolium iodide and the like; metal bromides such as lithium bromide, sodium bromide, potassium bromide, cesium bromide, and calcium bromide; bromide salts of quaternary ammonium compounds such as tetraalkylammonium bromide, and pyridinium bromide; metal complexes such as ferrocyanide salts, and ferricyanide ions; thiosulfates such as sodium thiosulfate, ammonium thiosulfate, potassium thiosulfate, and calcium thiosulfate; sulfites such as sodium sulfite, potassium sulfite, ammonium sulfite, iron sulfite, sodium bisulfite, and calcium sulfite; and mixtures thereof. Among these materials, tetrapropylammonium iodide is preferred.

The electrolytic concentration of the electrolyte is preferably 0.001 to 15 M.

Water, and polar solvent composed of a mixture of water and liquid buffering component may be used as the protic polar solvent. Aprotic polar solvents include nitriles such as acetonitrile ($CH_3CN$); carbonates such as propylene carbonate and ethylene carbonate, heterocyclic compounds such as 1,3-dimethyl-imidazolinone, 3-methyl-non-oxazolinyl, and dialkyl imidazolium salts; dimethyl formamide, dimethyl sulfoxide, sulfolane and the like. Among these aprotic polar solvents, acetonitrile is preferred. Aprotic polar solvents and protic polar solvents can be used individually or as a mixture thereof. The mixture of polar aprotic solvent and protic polar solvent is preferably a mixture of water and acetonitrile.

In step S1-2, the excitation light irradiates from the light source 13 on the electron acceptor surface 62a side toward the test substance 201 which is on the working electrode body 62. The type of excitation light may be suitably selected according to the type of labeled substance contained in the test substance. The amount of excitation light irradiation is preferably set in a range which suppresses noise generation.

In step S1-3, the transmitted excitation light is reflected by the reflective layer 80. The reflected light then irradiates the test substance 201 on the working electrode body 62. The test material 201 is thus excited.

In step S1-4, the photocurrent is measured by the previously mentioned ammeter 14 of the detection device 1. In step S1-4, the photocurrent measured value is transmitted to various processors. The A/D converter 16 digitally converts the photocurrent measured value (photocurrent value). the digitally converted photocurrent value is input to the controller 17. The controller 17 estimates the amount of test substance from the digitally converted photocurrent value based on a previously prepared calibration curve which represents the relationship between the photocurrent value and the amount of test substance. The controller 17 then creates a detection result screen to display the estimated amount of test substance on the display 2. Thereafter, the detection result screen created by the controller 17 is transmitted to the display 2. The display 2 displays the detection result screen. Subsequently, the process ends.

Note that in the detection device 1 used in the present embodiment the light source 13 is disposed on the electron acceptor surface 62a side of the inspection tip 20. In the inspection tip 20 used in the present embodiment, the reflective layer 80 is integratedly formed with the working electrode body 62 through the insulating layer 65.

However the disposition of the reflective part and the light source is not specifically limited to that described in the present embodiment. FIGS. 15 through 18 briefly show a modification of the disposition of the light source and reflective part in the photoexcitation irradiation step and the photoexcitation reflection step.

Figure 15:
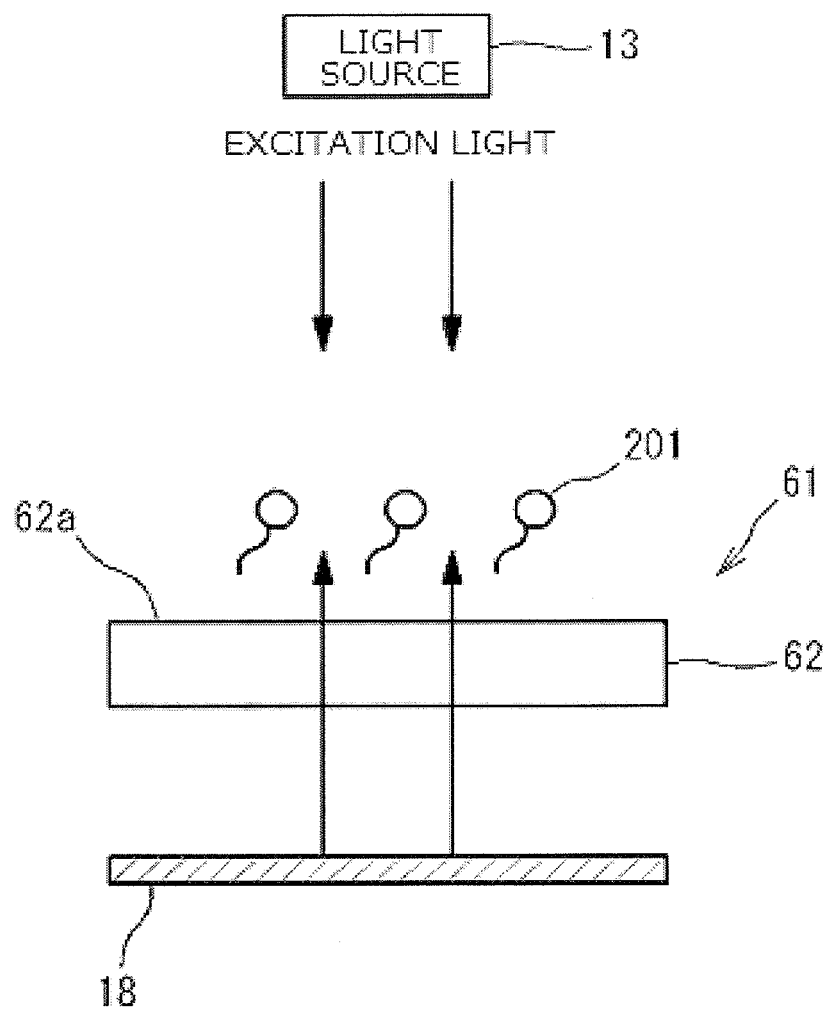
FIG. 15 briefly shows a modification of the placements of the light source and the reflecting part in the photoexcitation process and the photoexcitation reflection process.
Figure 16:
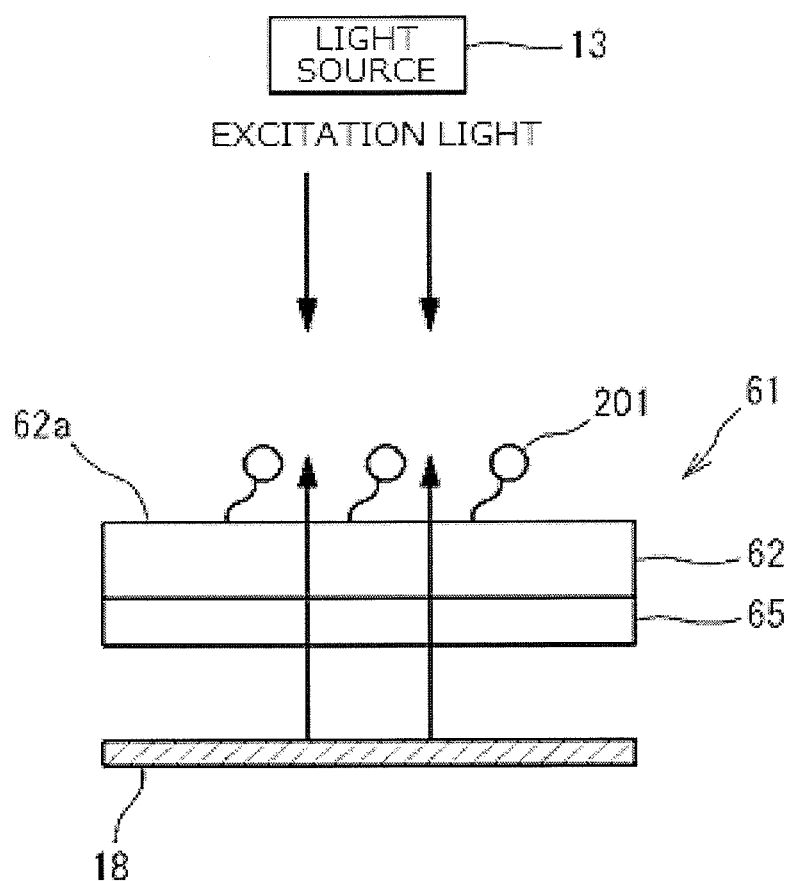
FIG. 16 briefly shows a modification of the placements of the light source and the reflecting part in the photoexcitation process and the photoexcitation reflection process.

In the detection device used in the modification shown in FIG. 15, the light source 13 is provided on the electron acceptor surface 62a side. In this detection device, the light source 13 is disposed at a position separated from the working electrode body 61. In the inspection tip used in the modification shown in FIG. 15, the reflective part 18 is provided on the surface on the opposite side from the electron acceptor surface 62a. The reflective part 18 is disposed at a position separated from the working electrode body 62. Note that in this modification an insulating layer 65 may be provided on the surface on the opposite side from the electron acceptor surface 62a in the working electrode body 62 (refer to FIG. 16).

Figure 17:
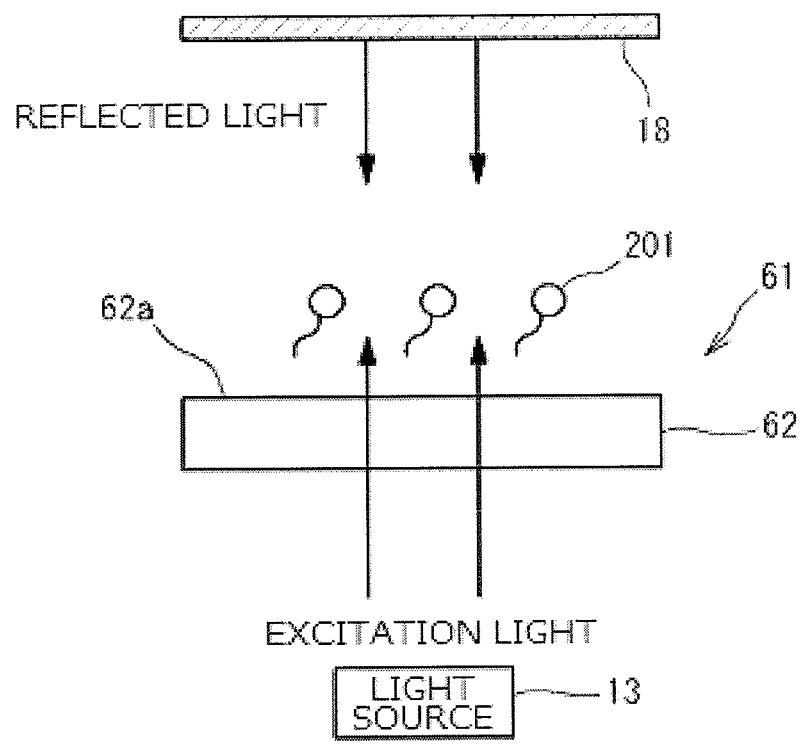
FIG. 17 briefly shows a modification of the placements of the light source and the reflecting part in the photoexcitation process and the photoexcitation reflection process.
Figure 18:
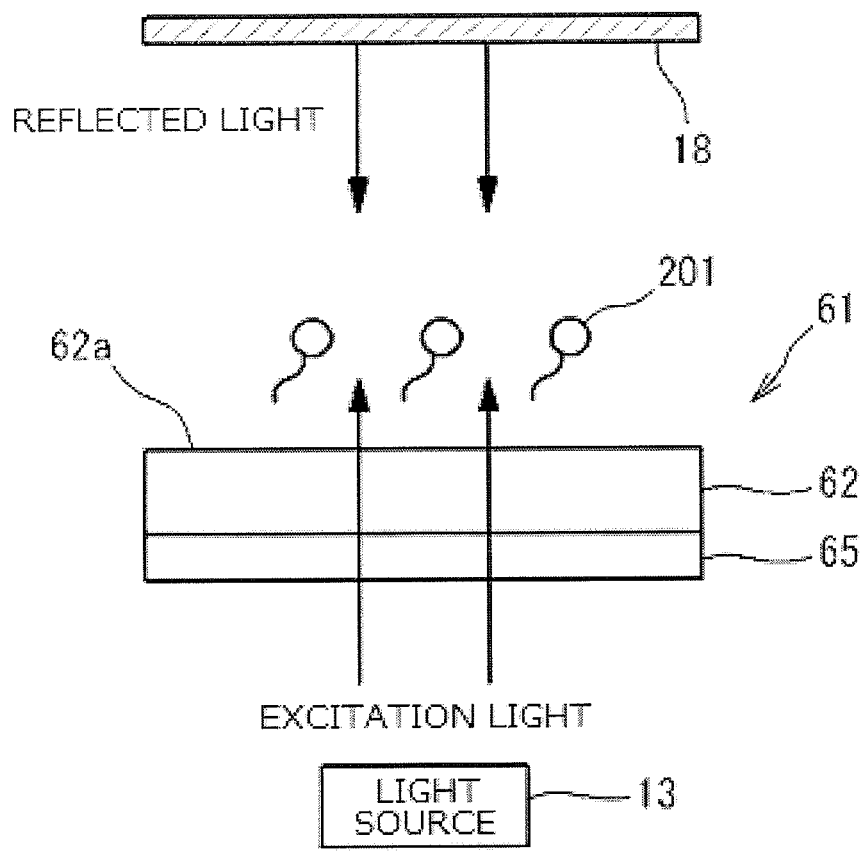
FIG. 18 briefly shows a modification of the placements of the light source and the reflecting part in the photoexcitation process and the photoexcitation reflection process.

In the detection device used in the modification shown in FIG. 17, the light source 13 is provided on the opposite side of the electron acceptor surface 62a. In the inspection tip, the reflective part 18 is disposed on the electron acceptor surface 62a side at a position separated from the working electrode body 62. Note that in this modification an insulating layer 65 may be provided on the surface on the opposite side from the electron acceptor surface 62a in the working electrode body 62 (refer to FIG. 18).

Figure 19:
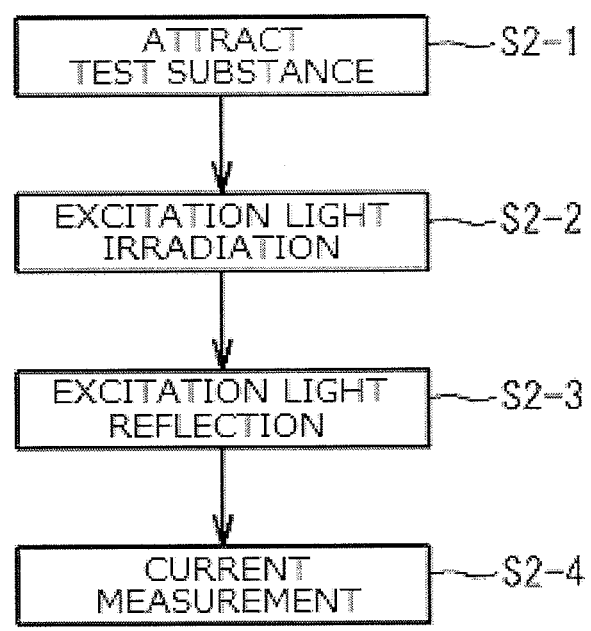
FIG. 19 is a flow chart showing the processing sequence of another embodiment of the method of detecting a test substance of the present invention.

The method 1-2 is described below referring to the drawings. FIG. 19 is a flow chart showing the processing sequence of another embodiment of the method of detecting a test substance of the present invention (method 1-2). FIG. 20 briefly shows each process of the embodiment of the method of detecting a test substance of the present invention (method 1-2).

In method 1-2, the user first injects a liquid sample containing a test substance from the previously mentioned sample injection inlet 30b of the inspection tip 20. Thus, the test substance 201 is attracted to the electrode body 62 without the presence of a capture substance (refer to FIGS. 20(A) and 20(B), and "test substance attraction step (step S2-1) in FIG. 19; equivalent to step (1-1)). In step S2-1, the test substance 201 is established on the working electrode body 62.

In step S2-1, for example, the user injects an attractant liquid from the previously mentioned sample injection inlet 30b of the inspection tip 20 to attract the test sample 201 onto the working electrode body 62. In this way the test substance 201 is attracted to a region of possible electron transport between the working electrode 61 without the presence of a capture substance.

In this case, "region of possible electron transport between the working electrode 61 without the presence of a capture substance" is usually a region 0 to 10 nm from the working electrode 61. In the present specification, "without the presence of a capture substance" means "substantially without the presence of a capture substance." That is, the concept of "without the presence of a capture substance" includes the slight presence of a capture substance to a degree that does not contribute substantial capture of the target substance on the working electrode.

Attraction of the test substance 201 on the working electrode 61 can be accomplished by hydrophobic interaction or hydrophilic interaction between the attractant liquid and the working electrode 61, or using an electrophoretic effect by applying a voltage to the working electrode 61 or the counter electrode 66.

The attraction process may be accomplished by, for example, 1) increasing the hydrophobic interaction or hydrophilic interaction between the test substance 201 and the working electrode 61 (attraction method 1);

2) increasing the electrophoretic effect by applying a positive or negative voltage to the working electrode 61 according to the load of the modified test substance 201 (attraction method 2). Attraction method 1 and attraction method 2 may be used individually or in combination.

In attraction method 1, when the test substance 201 contains nucleic acid (DNA, RNA), the attractant liquid preferably contains chaotropic ions from the perspective of increasing the hydrophobic interaction or hydrophilic interaction between the test substance 201 and the working electrode 61 to attract the test substance to the vicinity of the working electrode 61.

Chaotropic ions include, for example, iodide ion, bromide ion, guanidine ion, thiocyanate ion, tribromo acetic acid ion, trichloroacetic acid ion, perchlorate ion, dichloroacetic acid ion, nitrate ion, chloride ion, acetate ion, barium ion, calcium ion, lithium ion, cesium ion, potassium ion, magnesium ion and the like.

When the attractant liquid contains chaotropic ions, the concentration of the chaotropic ions in the attractant liquid will differ depending on the type of chaotropic ion used. The concentration is usually 1.0 to 8.0 mol/L. When the chaotropic ion used is guanidine ion, the concentration of chaotropic ion in the attractant liquid is usually 4.0 to 7.5 mol/L When the chaotropic ion used is cyanate ion, the concentration of the chaotropic ion in the attractant liquid is usually 3.0 to 5.5 mol/L.

Note that when the test substance 201 contains nucleic acid, the test substance 201 can be attracted to the vicinity of the working electrode 61 by conventional nucleic acid extraction and purification methods.

Nucleic acid extraction and purification methods include methods using a liquid phase, and methods using a carrier for nucleic acid binding. Examples of methods using a liquid phase include extraction with phenol/chloroform (Biochimica et Biophysica acta, 1963 issue, Vol 72, pp. 619-629), alkali method SDS (Nucleic Acid Research, published in 1979, 7 Volume, pp. 1513-1523), and nucleic acids precipitated with ethanol in buffer containing guanidine hydrochloride (Analytical Biochemistry, 162,1987,463) and the like. Examples of methods of using a carrier for nucleic acid binding include a method of nucleic acid isolation and adhering to glass particles using glass particles and sodium iodide solution (Proc. Natl. Acad. Sci. USA, 76-2: 615-619,1979), and a method using silica particles and chaotropic ions (e.g., J. Clinical. Microbiology, Issue 1990, Vol 28, pp. 495-503; JP Patent No. 2,680,462). In the method using chaotropic ions and silica particles, first, a sample is prepared by mixing the silica particles for binding nucleic acid with a solution containing chaotropic ions having the ability to release nucleic acid in a sample; the nucleic acid then binds to the silica particles. Next, the contaminants are removed by washing. Thereafter, the nucleic acid which was bound to the silica particles is recovered. According to this method, the nucleic acid can be rapidly and simply extracted. Moreover, this method not only extracts DNA, it also is suitable for extracting the more unstable RNA, and is very good in terms of obtaining nucleic acid of high purity.

In this case, when the test substance 201 contains nucleic acid, the test substance 201 can be attract to the vicinity of the working electrode 61 by using a liquid solvent as the attractant liquid in the nucleic acid extraction and purification. In this case, use of guanidinium ion, iodide ion, bromide ion, thiocyanate ion, or a combination thereof is preferred as the chaotropic ion, and use of an electrode for binding nucleic acid is preferred as the working electrode (for example, indium oxide containing tin).

When the test substance 201 contains nucleic acid, the attractant liquid may contain a buffer solution as necessary. The buffer solution may be a buffer solution that is commonly used to stably preserve nucleic acid. The buffer solution preferably has a buffering capacity in the neutral range, that is, a pH of 5.0 to 9.0, from the perspective of stably preserving the nucleic acid. Examples of useful buffering solutions include tris-hydrochloride, sodium tetraborate-hydrochloric acid, potassium dihydrogen phosphate-sodium tetraborate buffer and the like. The buffer solution concentration is preferably 1 to 500 mmo/L.

On the other hand, in attraction method 2, a positive or negative voltage is applied to the working electrode according to the load of the test substance 201. For example, when the test substance 201 contains nucleic acid, the nucleic acid portion in the test substance 201 has a negative charge. Therefore, the test substance 201 can be attracted to the vicinity of the working electrode 61 by applying a positive voltage to the working electrode 61.

After step S2-1, the user then sets the inspection tip 20 in the chip receiver 11 of the detection device 1. The user then starts the operation of the detection device 1. At this time, excitation light is irradiated toward the test substance 201 on the working electrode body 62 by the light source 13 of the detection device 1 (refer to "excitation light" in FIG. 20C and "photoexcitation irradiation step (step S2-2)" in FIG. 19; corresponds to step (S1-2)). The excitation light transmitted through the working electrode body 62 is reflected toward the test substance 201 on the working electrode body 62 by the reflective layer 80 of the working electrode 61 (refer to "reflected light" in FIG. 20C and "photoexcitation reflection step (step S2-3)" in FIG. 19; corresponds to step (1-3)). Thereafter, the photocurrent produced by photoexcitation of the test substance 201 is measured by the ammeter 14 of the detection device 1 (refer to "current measuring process (step S2-4) in FIG. 19; corresponds to step (1-4)).

Steps S2-2 through S2-4 are carried out in the presence of an electrolyte. Therefore, when using the liquid attractant in step S2-1, the attractant liquid is replaced in the electrolyte as necessary. Note that the attractant liquid has the property of supplying electrons to the labeled substance in an oxidized state, and this attractant liquid also may be used directly in the detection process when photoelectrochemical detection of the test substance is possible.

Steps S2-2 through S2-4 are carried out similar to steps S1-2 through S1-4 in method 1-1.

Note that in method 1-2, the working electrode is used without the presence of a capture substance to capture the test substance. Accordingly, the working electrode 61 can be washed in a simple process and reused. Washing the working electrode 61 is accomplished by an ultraviolet-ozone wash (UV-$O_{3<}$ wash) or the like. In a UV-$O_3$ wash, ultraviolet decomposition of organic compounds and decomposition of organic compounds by generation of $O_3$ and strong oxidizing action in the decomposition process remove such organic compounds from the surface of the electrode.

Further, when the test substance contains nucleic acid, the labeled test substance 240a is separated from the working electrode 51 by applying a negative voltage on the working electrode 51 in a suitable solution. This dissociation occurs because the nucleic acid is negatively charged. Examples of such useful solutions include phosphate buffered physiological saline (PBS), and TEB (composition: 10 mM tris-HCL buffer, 1 mM EDTA) water.

Note that in step S2-1 of method 1-2 a modified test substance can be used by adding an attractant modified substance to the test substance 201. Examples of attractant modified substances include DNA and RNA.

[Method of Detecting a Sample Substance]

The method of detecting a sample substance of the present invention is described below.

Figure 21:
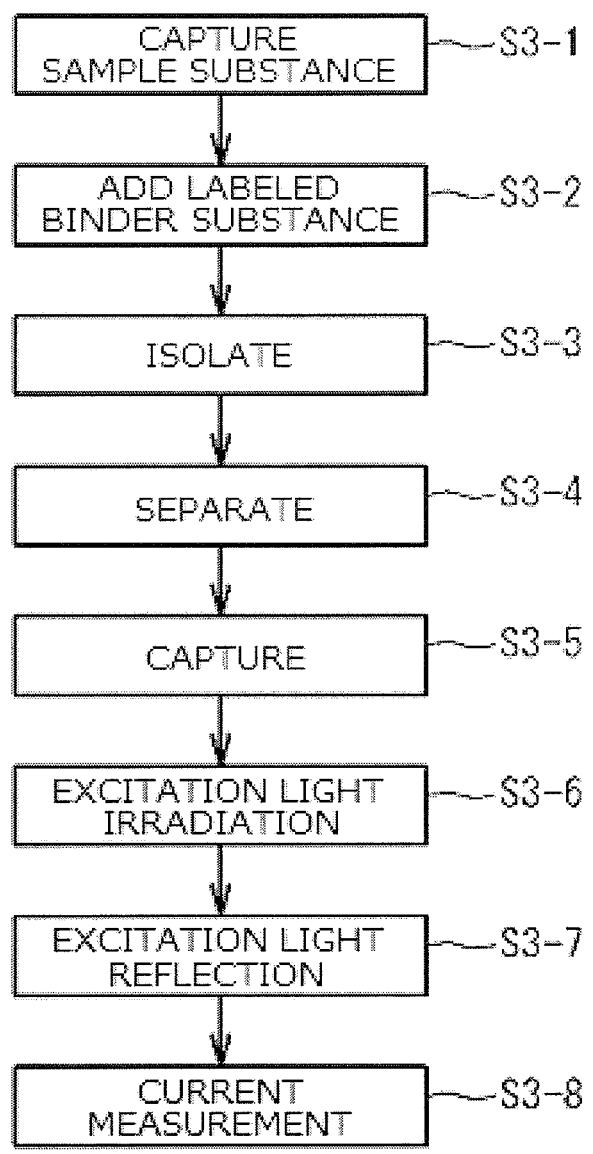
FIG. 21 is a flow chart showing the processing sequence of an embodiment of the method of detecting a sample substance of the present invention.

The method of detecting a sample substance of the invention is a method of photoelectrochemically detecting a sample substance using a transparent working electrode body and a counter electrode, comprising (2-1) a step of forming a composite body of sample substance and a labeled binder configured with the sample substance in contact with the labeled binder such that the sample substance is captured by the binding substance that is labeled with a labeling substance;

(2-2) a step of establishing at least the labeled substance on the working electrode;

(2-3) a step of irradiating excitation light on the labeled substance on the working electrode body;

(2-4) a step of reflecting the excitation light transmitted through the working electrode body toward the labeled substance on the working electrode body; and (2-5) a step of measuring the electrical current flowing between the working electrode body and the counter electrode. The processing sequence of the embodiment of the method of detecting a sample substance of the present invention (referred to as "method 2") is shown in FIG. 21. Although the detection device, inspection tip, and detection set described above are used in method 2, the present invention is not limited to this usage.

Figure 23:
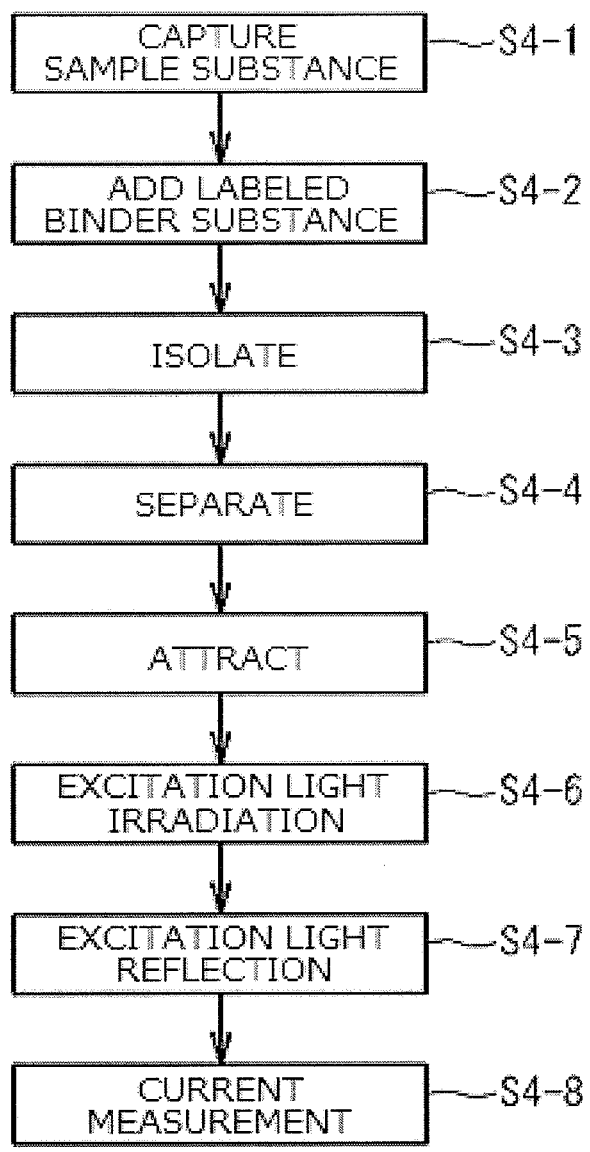
FIG. 23 is a flow chart showing the processing sequence of another embodiment of the method of detecting a sample substance of the present invention.

Method 2 is classified into method 2-1 and method 2-2 below according to the type of procedure performed in step (2-2). Method 2-1 is a method which uses a capture substance to capture the test substance (refer to FIG. 21). Method 2-2 is a method which attracts the test substance to the working electrode body (refer to FIG. 23).

Method 2-1 is first described below referring to the drawings. FIG. 21 is a flow chart showing the processing sequence of an embodiment of the method of detecting a sample substance of the present invention (method 2-1). FIG. 20 briefly shows each process of the embodiment of the method of detecting a sample substance of the present invention (method 2-1).

Method 2-1 corresponds to method 1-1. Method 2-1 differs from method 1-1 in that the steps below are included.

a step of capturing the sample substance in a solid phase for capturing the sample substance (sample substance capture process (step S3-1) in FIG. 21);

a step of adding to the sample substance a labeled binder substance which has been labeled with a labeled substance of binding substance to capture the sample substance (labeled binder substance adding process (step S3-2) in FIG. 21);

a step of isolating the solid phase containing the sample substance (isolation process (step S3-3)); and a step of separating at least the labeled substance from the solid phase according to the amount of sample substance (separation process (step S3-4) in FIG. 21). In this case, a sample substance is detected by the detection device 1 using the previously described inspection tip 20.

In method 2-1, the user first brings the sample substance S into contact with the solid phase 220 which captures the sample substance S (refer to step S3-1; FIG. 22A). Hence, the sample substance S is captured by the solid phase 220 (refer to FIG. 22B).

The solid phase 220 is configured of a solid phase body 230 which immobilizes a capture substance 221 to capture the sample substance S. The same substance as the capture substance 210 used in method 1-1 may be used as the capture substance 221. Note that the capture substance 221 used in the solid phase 220 and the capture substance used in the capture process (step S3-5) (described layer) may be substances of mutually different types, or may be substances having mutually different recognition sites in the sample substance.

The contact between the sample substance S and the solid phase 220 may be accomplished within a vessel, for example. The contact between the sample substance S and the solid phase 220 is carried out under conditions that bind the sample substance S to the capture substance 221. These conditions may be suitably selected according to the type of sample substance S and capture substance 221.

Thereafter, the user adds the labeled binder substance (test substance 201) to the solid phase 230 with the captured sample substance S (step S3-2). In this way a solid phase 231 is obtained which contains the composite of the sample substance S and the labeled binder substance (test substance 201)(refer to FIG. 22).

The addition of the labeled binder substance (test substance 201) to the solid phase 230 is carried out under conditions that bind the sample substance S to the labeled binder substance (test substance 201). These conditions may be suitably selected according to the type of sample substance S and labeled binder substance 201.

The user then isolates the solid phase 231 containing the composite, sample substance S, and labeled binder substance (test substance 201) (step S3-3).

In step S3-3, the isolation method of the solid phase 231 can be suitably selected according to the type of solid phase body 222. For example, when the solid phase body 222 is magnetic beads, the solid phase 231 may be drawn to a magnet. In this case, the solid phase 231 can be easily isolated using a magnet. When the solid phase body 222 is a substrate, components other than the sample substance S can be eliminated by replacing the solution on the substrate with fresh solution. In this case, the solid phase 231 can be easily isolated by replacing the solution.

Next, the user separates the labeled binder substance (test substance 201) from the solid phase 231 according to the amount of sample substance (step S3-4, refer to FIG. 22D).

In step S3-4, the user separates the labeled binder substance (test substance 201) according to the amount of sample substance using a separation method suited to the type of labeled binder substance (test substance 201) used in step S3-2. For example, when the sample substance S is nucleic acid and a labeled binder substance (test substance) is used that contains nucleic acid with a sequence that is complementary to the sample substance S, the labeled binder substance (test substance 201) can be easily separated from the solid phase 231 according to the amount of sample substance by heating the solution containing the composite formed on the solid phase body 222. When the composite of the sample substance S and the labeled binder substance (test substance 201) contains nucleic acid that can be cleaved, the labeled binder substance (test substance 201) or part thereof can be obtained according to the amount of sample substance S by cleaving the recognition sequence in the nucleic acid by a restriction enzyme.

Thereafter, the user injects the labeled binder substance (test substance 201) that was separated in step S3-4 from the sample injection inlet 30b of the inspection tip 20. The user then sets the inspection tip 20 in the tip receiver 11 of the detection device 1. The user then starts the operation of the detection device 1. The capture process (step S3-5), photoexcitation irradiation process (step S3-6), photoexcitation reflection process (step S3-7), and current measuring process (step S3-8) are carried out identically to the test substance capture process (step S1-1), photoexcitation irradiation process (step S1-2), photoexcitation reflection process (step S1-3), and current measuring process (step S1-4 in method 1-1. Note that in method 2-1 the labeled binder substance addition process also may be performed after the isolation process. Steps S3-1 through S3-4 may be carried out within the inspection tip 20.

Method 2-2 corresponds to method 1-2. Method 2-2 differs from method 1-2 in that the steps below are included.
- a step of capturing the sample substance in a solid phase for capturing the sample substance (sample substance capture process (step S4-1) in FIG. 23);
- a step of adding to the sample substance a labeled binder substance which has been labeled with a labeled substance of binding substance to capture the sample substance (labeled binder substance adding process (step S4-2) in FIG. 23);
- a step of isolating the solid phase containing the sample substance (isolation process (step S4-3) in FIG. 23); and
- a step of separating at least the labeled substance from the solid phase according to the amount of sample substance (separation process (step S4-4) in FIG. 23). These steps S4-1 through 4-4 are carried out identically to steps S3-1 through S3-4 in method 2-1.

Thereafter, the attraction process (step S4-5), photoexcitation irradiation process (step S4-6), photoexcitation reflection process (step S4-7), and current measuring process (step S4-8) are carried out identically to the test substance attraction process (step S2-1), photoexcitation irradiation process (step S2-2), photoexcitation reflection process (step S2-3), and current measuring process (step S2-4 in method 1-2. Note that in method 2-2 the labeled binder substance addition process also may be performed after the isolation process.

The method of detecting a sample substance of the invention is a method of photoelectrochemically detecting a sample substance which is photoelectrochemically active using a transparent working electrode body and a counter electrode, the method comprising
(3-1) a step of establishing the sample substance on the working electrode body;
(3-2) a step of irradiating excitation light on the sample substance on the working electrode body;
(3-3) a step of reflecting the excitation light transmitted through the working electrode body toward the sample substance on the working electrode body; and
(3-4) a step of measuring the current between the working electrode body and the counter electrode.

Figure 24:
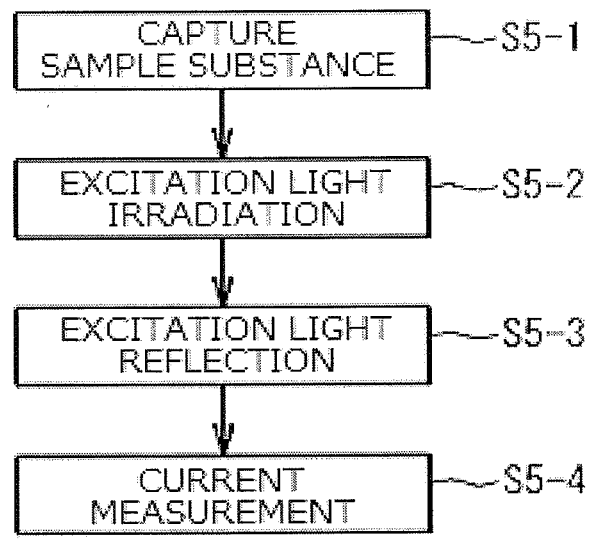
FIG. 24 is a flow chart showing the processing sequence of yet another embodiment of the method of detecting a sample substance of the present invention.
Figure 25:
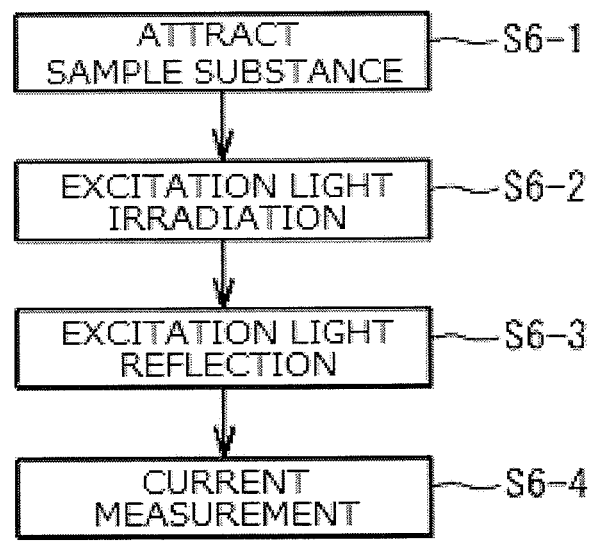
FIG. 25 is a flow chart showing the processing sequence of still another embodiment of the method of detecting a sample substance of the present invention.

Method 3 is classified into method 3-1 and method 3-2 below according to the type of procedure performed in step (3-1). Method 3-1 is a method which uses a capture substance to capture the sample substance (refer to FIG. 24). Method 3-2 is a method which attracts the sample substance to the working electrode body (refer to FIG. 25).

Methods 3-1 and 3-2 can be carried out when the sample substance is a photoelectrochemically active substance. The sample substance produces a current via photoexcitation. Therefore, methods 3-1 and 3-2 do not require the addition of a labeled binder substance to the sample substance as in methods 2-1 and 2-2. Methods 3-1 and 3-2 can thus be carried out identically by using a sample substance instead of the test substance in methods 1-1 and 1-2. That is, step S5-1 through step S5-4 in method 3-1 can be carried out by the same operations as in steps S1-1 through S1-4 of method 1-1 with the exception that a sample substance is used in place of the test substance in method 1-1. Step S6-1 through step S6-4 in method 3-2 can be carried out by the same operations as in steps S2-1 through S2-4 of method 1-2 with the exception that a sample substance is used in place of the test substance in method 1-2.

EXAMPLES

Although the present invention is described in detail below by way of examples, the present invention is not limited to these examples.

Fabrication Example 1

(1) Forming the Electrode and Reflective Part

Figure 26A:
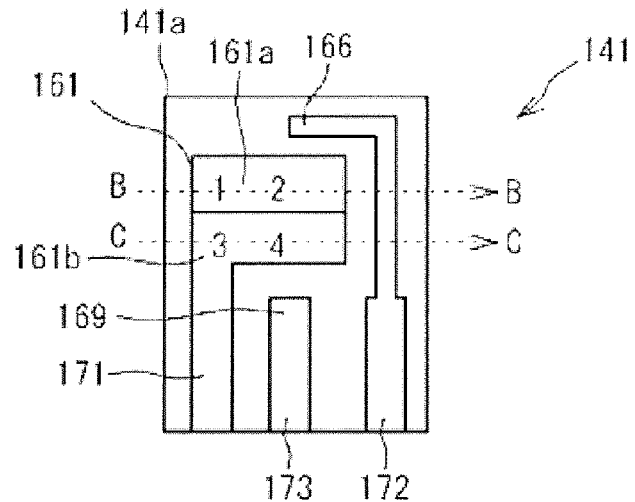
FIG. 26A briefly shows the structure of the working electrode of the electrode substrate provided in Fabrication Example 1.
Figure 26B:
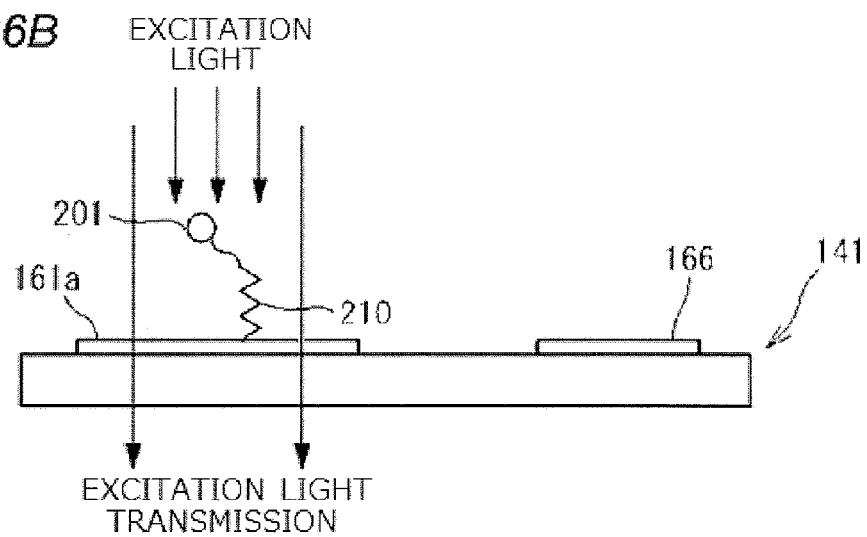
FIG. 26B is a cross sectional view on the B-B line of the electrode substrate in FIG. 26A.
Figure 26C:
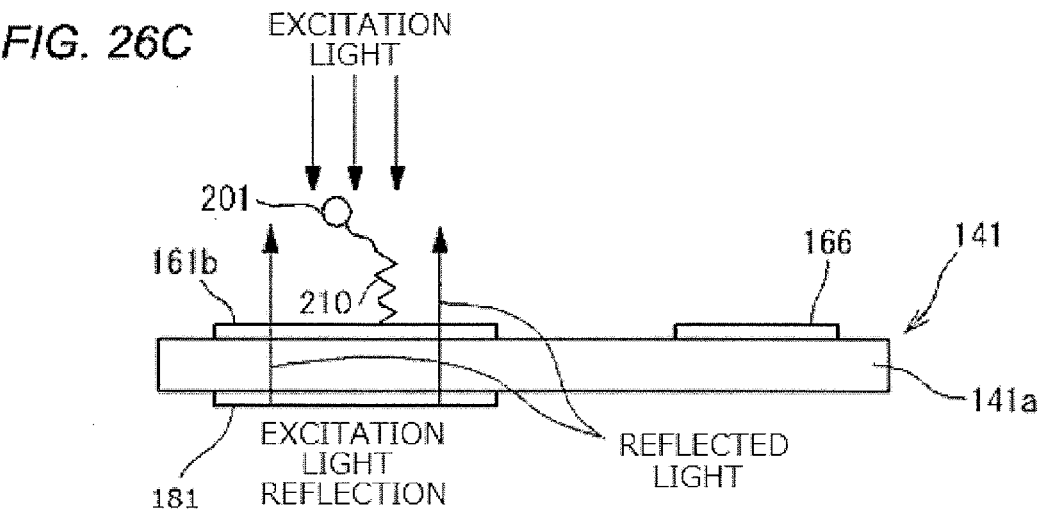
FIG. 26C is a cross sectional view on the C-C line of the electrode substrate in FIG. 26A.

A working electrode 161, which is composed of a thin film (approximately 200 nm in thickness) of indium oxide doped with tin, was formed on the surface of a substrate body 141a made of silicon dioxide (glass) via a sputtering method (refer to FIG. 26A). The thin film performs as both a conductive layer and an electron acceptor layer. Note that the working electrode 161 is divided into a first region 161a and a second region 161b. Then, using a sputtering method, a platinum thin film electrode 166 and a platinum thin film reference electrode 169 were formed on the same surface (referred to as "electrode surface" below) of the working electrode 161 on the substrate body 141a (refer to FIG. 26A). Thereafter, a platinum thin film reflective layer 181 was formed on the surface on the opposite side from the electrode surface of the substrate body 141*a* via spattering (refer to FIG. 26C). The reflective layer 181 was formed at a position corresponding to the second region 161*b* of the working electrode 161 so as to be the same size as the second region 161*b* of the working electrode 161. Excitation light passes through the first region 161*a* of the working electrode 161 (refer to FIG. 26B). The excitation light transmitted through the working electrode 161 in the second region 161*b* of the working electrode 161 is reflected by the reflective surface 181 toward the test substance on the second region 161*b* of the working electrode 161 (refer to FIG. 26C)

(2) Silane Coupling Treatment

The substrate body 141*a* obtained in (1) above was immersed for 1 hour in a silane coupling agent solution (1% vol APTES content toluene solution). The substrate body 141*a* was then removed and washed twice in toluene. Thereafter, the substrate was heated at 110° C. for 10 minutes to bind the APTES to the surface of the substrate body 141*a*. The substrate body 141*a* was immersed in toluene and subjected to ultrasonic cleaning for 10 minutes. Ultrasonic cleaning was performed 3 times. Then, the substrate body 141*a* was dehydrated with ethanol to bind the unbound APTES to the surface of the substrate. The residual ethanol was removed with a blower.

(3) Immobilizing the Capture Substance

An aqueous solution containing a DNA capture probe as a capture substance (100 μM DNA), and a UV crosslinking reagent (product name: microarray crosslinking reagent D; manufactured by GE Healthcare UK, Ltd.) were mixed in a 1:9 ratio (volume ratio) to obtain a 10 μM probe solution. 6 μL of the obtained probe solution was dripped on the surfaces of the working electrodes 161*a* and 161*b* Then, a UV irradiation device (product name: UV Crosslinker) irradiated the working electrodes 161*a* and 161*b* with 160 mJ/cm$^2$ ultraviolet light. In this way the DNA capture probe was fixed on the surface of the working electrodes 161*a* and 161*b*. The surfaces of the working electrodes 161*a* and 161*b* were then washed with ultra pure water. The ultra pure water remaining on the surface of the working electrodes 161*a* and 161*b* was later removed with a blower.

(4) Removal of Unfixed DNA Probe

There is a possibility of unfixed DNA capture probe remaining on the surface of the working electrodes 161*a* and 161*b* by just the operation performed in (3) above. Hence, the process below was performed to remove unfixed DNA capture probe.

Silicone rubber was arranged as a partition (thickness 0.1 mm) to circumscribe the substrate body 141*a*. 6 μL of a hybridization solution was injected into the space formed by the silicone rubber. Note that the hybridization solution was obtained by mixing ultra pure water and a hybridization buffer (product name: 2× hybridization buffer; manufactured by Affymetrix) in a 1:1 ratio (volume ratio). Then, the silicone rubber was covered with a cover glass to prevent evaporation. The substrate body 141*a* was then allowed to stand for 1 hour at 45° C. Next, the substrate body 141*a* was washed using a wash buffer (product name: Wash buffer A; manufactured by Affymetrix) and ultra pure water. The ultra pure water remaining on the surface of the substrate body 141*a* was later removed with a blower.

Fabrication Example 2

Acetonitrile (AN) and ethylene carbonate (EC) were mixed in a ratio of 2:3 (AN:EC (volume ratio)). The resulting mixture, and tetrapropylammonium iodide as an electrolyte salt was dissolved in the obtained mixture to obtain a concentration of 0.6M. Then, the resulting mixture, and iodine as an electrolyte, was dissolved so that its concentration is 0.06M. In this way an electrolyte solution was obtained.

Test Example 1

(1) Test Substance Capture

Silicone rubber (thickness 0.2 mm) was arranged as a partition to circumscribe the working electrodes 161*a* and 161*b* of the electrode substrate 141 obtained in fabrication example 1. A hybridization chamber was the installed on the electrode substrate 141. 20 μL of the hybridization solution was injected into the space formed by the chamber, the silicon rubber and electrode substrate 141. Note that the hybridization solution was obtained by adding target DNA (test substance) labeled with Alexa Fluor 750 labeling substance to the hybridization buffer (product name: 2× Hybridization buffer; manufactured by Affymetrix) to a concentration of 0 nM or 1 nM. The chamber injection inlet was sealed with a cover to prevent solution evaporation. Hybridization was carried out by allowing the chamber to stand for 1 hour at 45° C. Next, the substrate body 141*a* was washed using a wash buffer (product name: Wash buffer A; manufactured by Affymetrix) and ultra pure water. The ultra pure water remaining on the surface of the substrate body 141*a* was later removed with a blower.

(2) Measuring Photocurrent

An interval holding member of silicone rubber (thickness 0.2 mm) circumscribed the working electrodes 161*a* and 161*b* of the electrode substrate 141 after performing the process of (1) above. 12.5 μL of electrolyte obtained in fabrication example 2 was injected into the space formed by the silicone rubber. In this way the electrolyte was brought into contact with the working electrode, counter electrode, and reference electrode.

Figure 27:
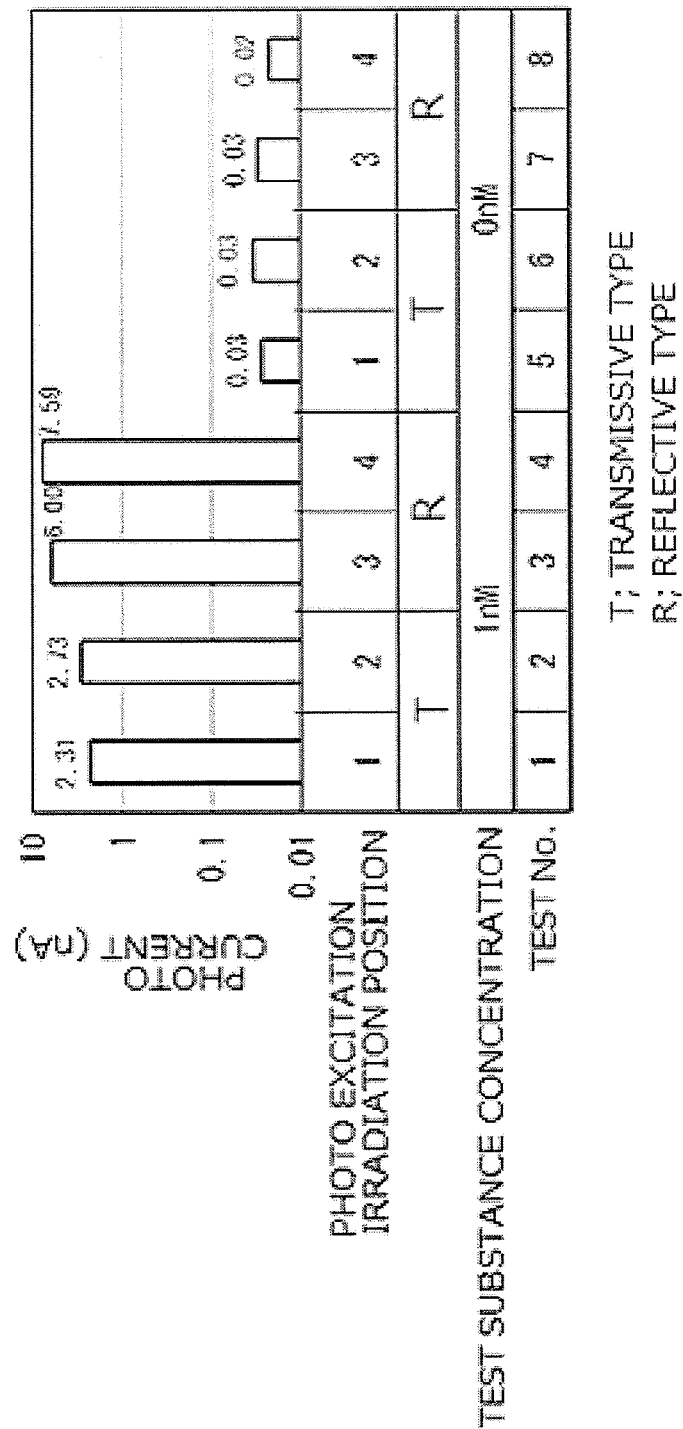
FIG. 27 is a graph showing the results of the examining the relationship between the photocurrent and the type of electrode (transmissive and reflective types) used in Test Example 1.

A cover glass was used as a cover to seal the space from above the electrode substrate 141. In this way the electrolyte leakage and evaporation were prevented. A voltage of 0 V was applied to the reference electrode as a standard relative to the working electrodes 161*a* and 161*b*. Excitation light (laser light; wavelength of 781 nm; photoexcitation intensity 13 mW) was irradiated at specific positions (irradiation positions 1 through 4 in FIG. 26) on the working electrodes 161*a* and 161*b*. The laser light flashed (ON/OFF) with predetermined period (1 Hz), and the photocurrent flowing between the counter electrode and either the working electrode 161*a* or working electrode 161*b* was measure. FIG. 27 shows the results of examining the relationship between the photocurrent and the type of electrode (transmissive and reflective types) used in Test Example 1. Note that "transmissive type" in FIG. 27 is the working electrode 161*a*. The "reflective type" is the working electrode 161*b*.

It can be understood from the results shown in FIG. 27 that when the test substance concentration is 1 nM, the photocurrent of tests 3 and 4 (reflective type) increased markedly compared to the photocurrent of tests 1 and 2 (transmissive type). When the test substance concentration was 0 nM, the photocurrent of tests 3 and 4 (reflective type) was identical to the photocurrent of the tests 1 and 2 (transmissive type). It can be understood from these results that the photocurrent can be markedly increased by reflecting the light transmitted through the working electrode toward the test substance on the working electrode.

Test Example 2

Operations identical to those of test example 1 were performed and photocurrent measured with the exception that the first region 161a of the working electrode 161 was irradiated with laser light with an intensity of 5.67 mW or 10.91 nm, and the second region 161b of the working electrode 161 was irradiated excitation light (laser light) with an photoexcitation intensity of 5.67 mW. The S/N ratio was then calculated. Note that the S/N ratio was calculated based on equation (I) below.

[(photocurrent when test substance concentration is 1 nM)−(photocurrent when test substance concentration is 0-nM)]/(photocurrent when test substance concentration is 0 nM)  [Eq. 1]

Figure 28A:
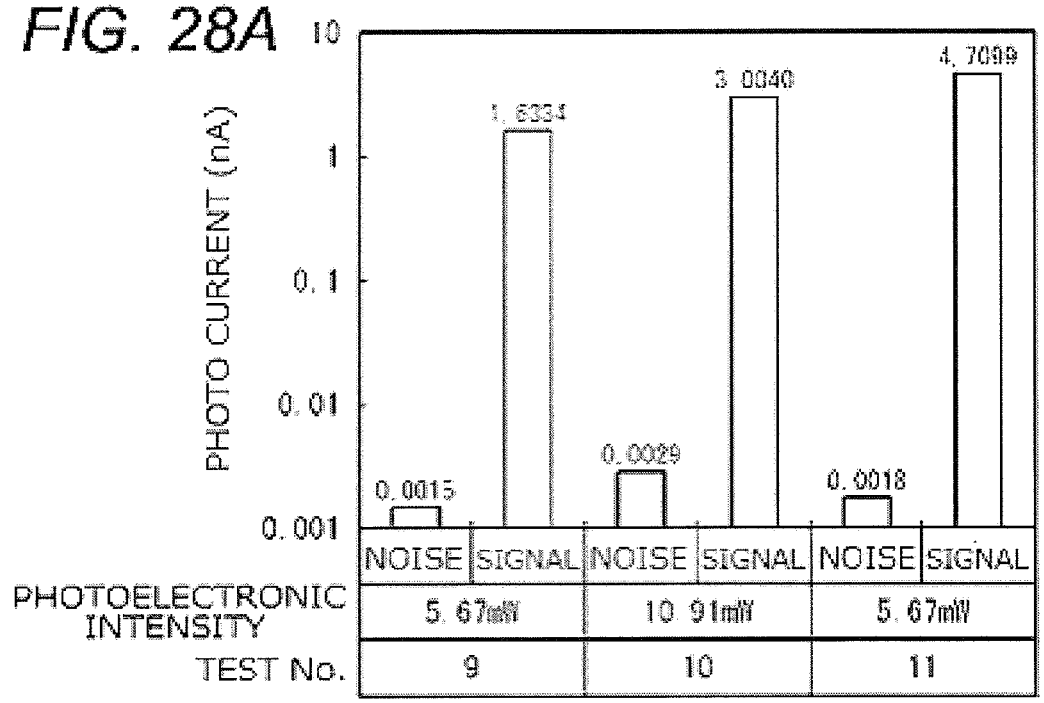
FIG. 28A is a graph showing the results of the examining the relationship between the photocurrent, the type of electrode used, and the photoexcitation intensity in Test Example 2.

FIG. 28A shows the results of examining the relationship between the photocurrent, photoexcitation intensity, and the type of electrode used in Test Example 2. Test 9 pertained to measured photocurrent when laser light (excitation light) of photoexcitation intensity of 5.67 mW irradiated the working electrode 161a (transmissive type). Test 10 pertained to measured photocurrent when laser light (excitation light) of photoexcitation intensity of 10.91 mW irradiated the working electrode 161a (transmissive type). Test 11 pertained to measured photocurrent when laser light (excitation light) of photoexcitation intensity of 5.67 mW irradiated the working electrode 161b (reflective type). Note that "noise" was the photocurrent when the test substance concentration was 0 nM (that is, noise not origination in the test substance). The "signal" was the photocurrent when the test substance concentration was 1 nM (that is, signal originating in the test substance).

It can be understood from the results shown in FIG. 28A that the photocurrent in the case of "signal" in test 10 is about double the photocurrent in the case of "signal" in test 9. It can be understood from the results shown in FIG. 28A that the photocurrent in the case of "noise" in test 10 is about double the photocurrent in the case of "noise" in test 9. It can be concluded from these results that the signal originating in the test substance and the noise that does not originate in the test substance increase when the photoexcitation intensity is increased.

It can be understood from the results shown in FIG. 28A that the photocurrent in the case of "signal" in test 11 is about 2.6 times the photocurrent in the case of "signal" in test 9. It can be understood from the results shown in FIG. 28A that the photocurrent in the case of "noise" in test 11 is about the same as the photocurrent in the case of "noise" in test 9. Hence, it can be concluded from these results that the generation of noise that does not originate in the test substance can be unexpectedly suppressed regardless of the increase of the signal originating in the test substance when a working electrode with a reflective part is used.

Figure 28B:
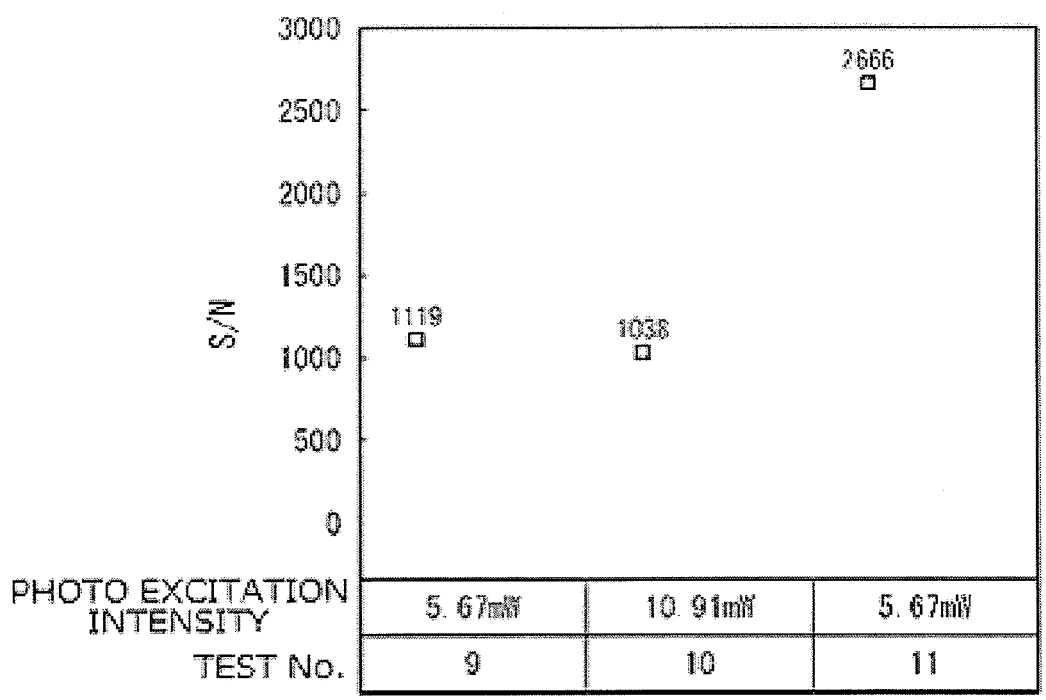
FIG. 28B is a graph showing the results of the examining the relationship between the S/N ratio, the type of electrode used, and the photoexcitation intensity in Test Example 2.

The S/N ratio was then calculated based on the results shown in FIG. 28A. FIG. 28B shows the results of examining the relationship between the S/N ratio, photoexcitation intensity, and the type of electrode used in Test Example 2.

It can be understood from the results shown in FIG. 28B that the S/N ratio in the case of test 11 is greater than the S/N ratio in the case of test 9. However, the S/N ratio in the case of test 10 is less than the S/N ratio in the case of test 9. Hence, it can be concluded from these results that detection sensitivity is improved when using a working electrode with a reflective part.

Fabrication Example 3

The electrodes and reflective part were formed identically to the method described in fabrication example 1(1), with the exception that a reflective layer 181 configured by a thin gold film (50.9 nm in thickness) was formed by vapor deposition. Thereafter, an electrode substrate 141 was obtained by coating with a silane coupling agent, fixing a capture material, and removing the unfixed DNA probe identically to the method described in fabrication example 1(2)-(4) (refer to FIG. 26A).

Test Example 3

The test substance capture and photocurrent measurement were carried out identically to the method described in test example 1(1) and (2), with the exception that the hybridization solution obtained by adding target DNA (test substance) labeled with Alexa Fluor 750 labeling substance to the hybridization buffer (product name: 2× Hybridization buffer; manufactured by Affymetrix) to a concentration of 0 nM or 10 nM was used, and the electrode substrate 141 obtained by fabrication example 3 was used. The obtained results are shown in FIG. 29.

Figure 29:
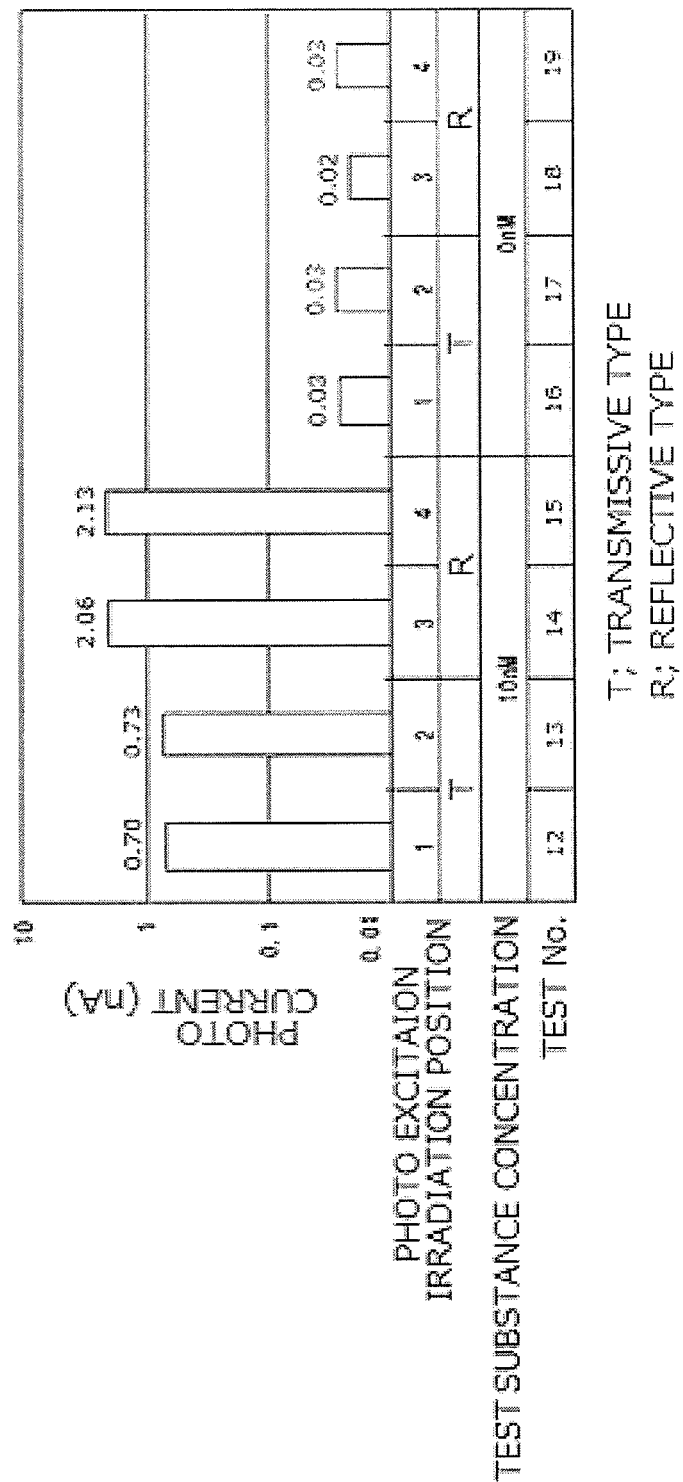
FIG. 29 is a graph showing the results of the examining the relationship between the photocurrent and the type of electrode (transmissive and reflective types) used in Test Example 3.

It can be understood from the results shown in FIG. 29 that when the test substance concentration is 10 nM, the photocurrent of tests 14 and 15 (reflective type) increased markedly compared to the photocurrent of tests 12 and 13 (transmissive type). When the test substance concentration was 0 nM, the photocurrent of tests 18 and 19 (reflective type) was substantially identical to the photocurrent of the tests 16 and 17 (transmissive type). These results confirm that it is possible to increase just the photocurrent originating from the dye by reflecting the light transmitted through the working electrode back toward the test substance on the working electrode.

Test Example 4

Figure 30A:
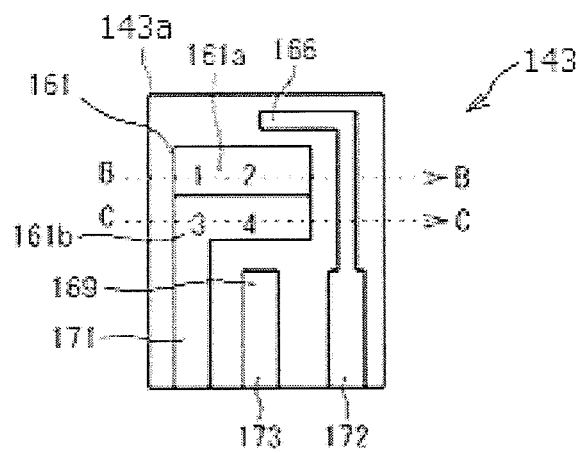
FIG. 30A briefly shows the structure of the working electrode of the electrode substrate used in Test Example 4.
Figure 30B:
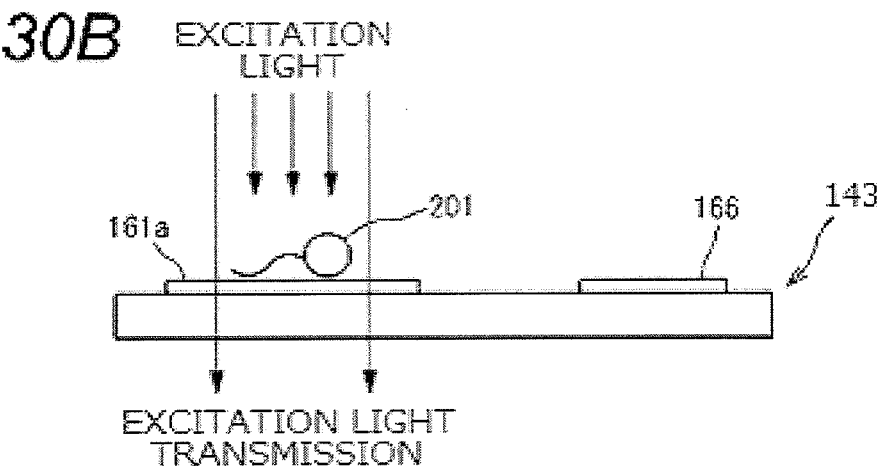
FIG. 30B is a cross sectional view on the B-B line of the electrode substrate in FIG. 30A.
Figure 30C:
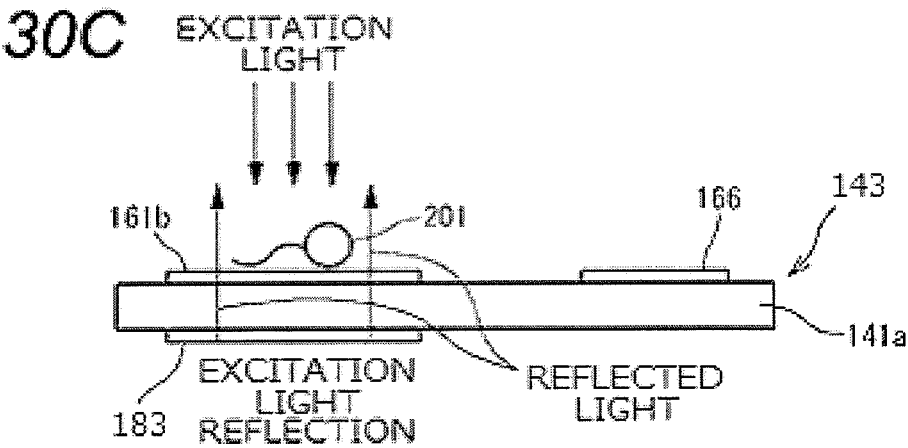
FIG. 30C is a cross sectional view on the C-C line of the electrode substrate in FIG. 30A.

The electrodes and reflective part were formed identically to the method described in fabrication example 1(1), with the exception that the reflective layer 183 configured by aluminum was formed by adhering aluminum foil to the back surface of the substrate 143a. Note that in test example 4, the electrode substrate 143 was obtained (refer to FIG. 30A) by washing the electrode surface for 10 minutes using a UV/O₃ (Model UV-1, Samco) instead of performing the operations of coating with the silane coupling agent, fixing the capture substance, and removing the unfixed DNA probe in fabrication example 1(2)-(4).

An interval holding member of silicone rubber (thickness of 0.2 mm) circumscribed the perimeter of the working electrodes 161a and 161b of the obtained electrode substrate 143. Then, 12.5 μL of a solution containing the target DNA probe (test substance) labeled with Alexa Fluor 750 labeling substance in the electrolyte solution of fabrication example 2 to obtain a concentration of 0 nM or 1 nM was injected into the space formed by the silicone rubber. In this way the same electrolyte was brought into contact with the working electrode, counter electrode, and reference electrode. A cover glass was used as a cover to seal the space from above the electrode substrate 143. Hence, leakage and drying of the electrolyte was prevented during photocurrent measurement.

Figure 31:
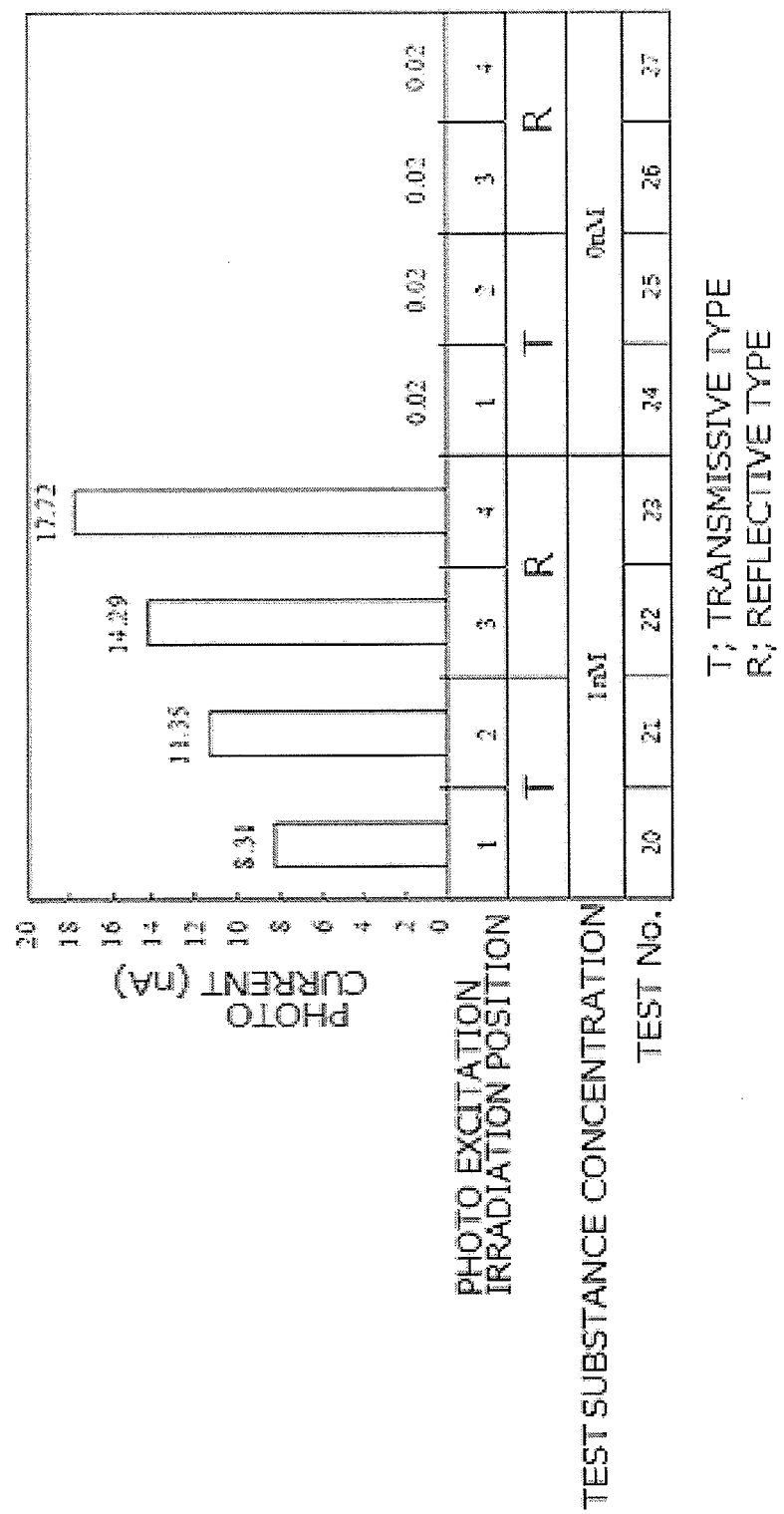
FIG. 31 is a graph showing the results of the examining the relationship between the photocurrent and the type of electrode (transmissive and reflective types) used in Test Example 4.

Thereafter, the photocurrent was measured identically to the method described in test example 1. The obtained results are shown in FIG. 31. It can be understood from the results shown in FIG. 31 that when the test substance concentration is 1 nM, the photocurrent of tests 22 and 23 (reflective type) increased markedly compared to the photocurrent of tests 20 and 21 (transmissive type). When the test substance concentration was 0 nM, the photocurrent of tests 26 and 27 (reflective type) was substantially identical to the photocurrent of the tests 24 and 25 (transmissive type). These results confirm that it is possible to increase just the photocurrent originating from the dye by reflecting the light transmitted through the working electrode back toward the test substance on the working electrode.

What is claimed is:

1. A detection device which photoelectrochemically detects a test substance that releases electrons by photoexcitation, comprising:
    an optically permeable working electrode body which accepts electrons from the test substance;
    a counter electrode;
    a light source which irradiates excitation light on the test substance on the working electrode body;
    a reflective part which reflects the excitation light that is emitted from the light source;
    wherein the reflective part is provided separately from the counter electrode and is provided at a position where the reflective part reflects the excitation light which passes through the working electrode body, toward the test substance on the working electrode body;
    wherein the detection device produces an increased signal while suppressing an increase in noise, as compared to when the excitation light transmitted through the working electrode body is not reflected, and
    the counter electrode is provided at a position where the excitation light emitted from the light source is not irradiated.

2. The detection device of claim 1, wherein
the reflective part comprises at least one metal selected from a group including platinum, aluminum, gold, silver, and copper.

3. The detection device of claim 1, wherein
the working electrode body comprises a conductive layer and an electron acceptor layer.

4. The detection device of claim 1, wherein
the light source is disposed on the electron acceptor layer side to accept electrons from the test substance on the working electrode body; and
the reflective part is provided on the opposite side from the electron acceptor layer.

5. The detection device of claim 4, wherein
the reflective part is provided at a position separated from the working electrode body.

6. The detection device of claim 4, wherein
the reflective part is formed on the substrate body which maintains the shape of the working electrode body.

7. The detection device of claim 4, wherein
the reflective part is integratedly formed with the working electrode body through an optically permeable insulation layer.

8. The detection device of claim 7, wherein
the optically permeable insulation layer is formed on the opposite surface from the electron acceptor layer in the working electrode body.

9. The detection device of claim 7, wherein
the insulation layer is a substrate body which maintains the shape of the working electrode body.

10. The detection device of claim 1, wherein
the light source is disposed on the opposite side from the electron acceptor layer which accepts electrons from the test substance on the working electrode body; and
the reflective part is provided at a position separated from the working electrode body on the electron acceptor layer side.

11. The detection device of claim 1, wherein
the optically permeable insulation layer is formed on the opposite surface from the electron acceptor layer in the working electrode body.

12. The detection device of claim 1, wherein
the light source is a laser.

13. A detection device which photoelectrochemically detects a test substance that releases electrons by photoexcitation, comprising:
    a light source which irradiates excitation light;
    a substrate including a first side from which the excitation light emitted from the light source passes into the substrate and a second side which is opposite to the first side;
    wherein the first side includes a first area where the excitation light is irradiated and a second area where the excitation light is not irradiated;
    an optically permeable working electrode which is formed within the first area and accepts electrons from the test substance on the working electrode;
    a counter electrode which is formed within the second area; and
    a reflective part which is formed on the second side and reflects the excitation light that passed through the working electrode toward the test substance on the working electrode, wherein the detection device produces an increased signal while suppressing an increase in noise, as compared to when the excitation light transmitted through the working electrode is not reflected.

14. The detection device of claim 13, wherein
the reflective part comprises at least one metal selected from a group including platinum, aluminum, gold, silver, and copper.

15. The detection device of claim 13, wherein
the working electrode comprises a conductive layer and an electron acceptor layer.

16. The detection device of claim 13, wherein
the light source is disposed so as to irradiate the excitation light toward the first side.

17. The detection device of claim 13, wherein
the light source is a laser.

* * * * *